US005843462A

United States Patent [19]
Conti-Fine

[11] Patent Number: 5,843,462
[45] Date of Patent: Dec. 1, 1998

[54] DIPHTHERIA TOXIN EPITOPES

[75] Inventor: Bianca M. Conti-Fine, Minneapolis, Minn.

[73] Assignee: Regents of The University of Minnesota, Minneapolis, Minn.

[21] Appl. No.: 564,972

[22] Filed: Nov. 30, 1995

[51] Int. Cl.$^6$ .......................... A61K 39/05; A61K 39/02; A61K 31/735; C07H 21/04
[52] U.S. Cl. ..................... 424/245.1; 424/184.1; 424/166.1; 424/236.1; 424/238.1; 424/234.1; 530/300; 530/350; 530/324; 530/325; 530/326; 530/327; 530/329; 530/328
[58] Field of Search .............................. 424/166.1, 184.1, 424/236.1, 245.1, 238.1, 234.1; 530/300, 324–329, 350

[56] References Cited

U.S. PATENT DOCUMENTS

| 4,830,962 | 5/1989 | Gelfand et al. . |
| 4,950,740 | 8/1990 | Greenfield et al. . |
| 5,158,884 | 10/1992 | Conti-Tronconti et al. ............ 435/240 |

FOREIGN PATENT DOCUMENTS

| 9321769 | 11/1993 | WIPO . |
| 9325210 | 12/1993 | WIPO . |

OTHER PUBLICATIONS

Bell, C.E., et al., "Crystal Structure of Diphtheria Toxin Bound to Nicotinamide Adenine Dinucleotide", *Biochemistry*, 35, pp. 1137–1149, (1996).
Choe, S., et al., "The Crystal Structure of Diphtheria Toxin", *Nature*, vol. 357, pp. 216–222, (May 21 1991).
Cieplak, W., et al., "Specific Cleavage of Diphtheria Toxin by Human Urokinase", *Biochemical and Biophysical Research communications*, vol. 157, No. 2, pp. 747–754, (1988).
Fu, H., et al., "Receptor binding domain of diphtheria toxin as a potential immunogen", *Vaccines 93*, pp. 379–383, (1993).
Giannini, G., et al., "The amino acid sequence of two non–toxic mutants of diphtheria toxin: CRM45 and CRM197", *Nucleic Acids Research*, Vo. 12, No. 10, pp. 4063–4069, (1994).
Greenfield, L., et al., "Mutations in Diphtheria Toxin Separate Binding from Entry and Amplify Immunotoxin Selectivity", *Science*, vol. 238, pp. 437–584, (Oct. 23, 1987).
Kaczorek, M., et al., "Nucleotide sequence and Expression of the Diphtheria tox228 Gene in *Escherichia coli*", *Science*, vol. 221, pp. 855–858, (Aug. 26, 1983).
Killen, K.P., et al., "Reversion of recombinant toxoids: mutations in diphtheria toxin that partially compensate for active–site deletions", *Proc. Natl. Acad. Sci., USA*, vol. 89, pp. 6207–6209, (Jul. 1992).
Ratti, G., et al., "The complete nucleotide sequence of the gene coding for diphtheria toxin in the corynophage omega (tox+) genome", *Nucleic Acids Research*, vol. 11, No. 19, pp. 6589–6595, (1983).

Rolf, J.M., et al., "Structure–function analyses of diphtheria toxin by use of monoclonal antibodies", *Infection and Immunity*, vol. 61, No. 3, pp. 994–1003, (1993).
Silverman, J.A., et al., "Structure–function relationships in diphtheria toxin channels: I. Determining a minimal channel–forming domain", *J. Membrane Biology*, 137, pp. 17–28, (1994).
Zucker, D.R., et al., "Monoclonal antibody analysis of diphtheria toxin–I. localization of epitopes and neutralization of cytotoxicity", *Molecular Immunology*, vol. 21, No. 9, pp. 785–793, (1984).
Falmagne et al, BBA, 827:45–50, 1985.
Choe et al, 1992, Nature 357:216–222.
Rolf et al 1991. Abstract #B–296. ASM 1991 Mtg. p. 75.
Eskola et al 1985. Lancet. May 25, 1995 pp. 1184–1186.
Silverman et al, 1994, J. Membrane Biol, 137;17–28.
Lerner et al, 1993, In: Biology of Immunological Disease pp. 331–338 Ed. Dixon et al.
Ada. 1989, In: Fundamental Immunol. $2^{nd}$ Ed. Editors, Paul pp. 985–1011.
Ratti et al, Nucleic Acid Res. 11(19):6589–6595.
Fue et al, Vaccines 1993 pp. 379–383.
Tortoulla et al, 1995, JBC. 270(46):27439–445.
Rolf et al, 1993, Infection Imm. 61(3):994–1003.
Raju et al, 1995. Eur. J. Immunol, 25:3207–3214.
Zucker et al, 1984. Mol. Immunol. 21(9):785–793.
Arnon, 1986, ThBS. 11:521–524.
Rolf et al 1990. JBC. 265(13):7331–7337.
Collier, R. J., et al., "Diphtheria Toxin: Mode of Action and Structure," *Bacteriol. Rev.*,39, 54–85 (1975).
Collier, R. J., et al., "Structure and Activity of Diphtheria Toxin—I. Thiol–Dependent Dissociation of a Fraction of Toxin into Enzymatically Active and Inactive Fragments," *J. Biol. Chem.*, 246, 1496–1503 (1971).
Collier, R. J., et al., "Structure and Activity of Diphtheria Toxin," In: *ADP Ribosylation Reactions: Biology and Medicine*, Hayaishi, O., et al., (eds.), Academic Press, Inc., New York,pp. 575–592 (1987).
Demotz, S., et al., "Delineation of Several DR–Restricted Tetanus Toxin T Cell Epitopes," *J. Immunol.*, 142, 394–402 (1989).
Greenfield, et al., "Nucleotide Sequence of the Structural Gene for Diphtheria Toxin Carried by Cornebacteriophage β," *Proc. Natl. Acad. Sci. USA*, 80, 6863–6857 (1993).
Ellis, R. W., et al., "New Technologies for Making Vaccines," In: Vaccines, Plotkin, S. A., et al., (eds.), W. B. Saunders Co., Philadelphia, pp. 568–575 (1988).
Etlinger, H. M., et al., "The Use of Recombinant Proteins and Synthetic Peptides in the Development of a *Plasmodium falciparum* Malaria Vaccine," In: *Modern Vaccinology*, Kurstak, E., (ed.), Plenum Medical Book Co., New York, pp. 341–356 (1994).

(List continued on next page.)

Primary Examiner—Nita Minnifield
Attorney, Agent, or Firm—Schwegman, Lundberg, Woessner & Kluth, P.A.

[57] ABSTRACT

A method for identifying an immunodominant sequence region in a diphtheria toxin-specific peptide is provided. Also provided are diphtheria toxin specific peptides with an immunodominant sequence region.

15 Claims, 7 Drawing Sheets

OTHER PUBLICATIONS

Manfredi, A. A., et al., "Human Acetylocholine Receptor Presentation in Myasthenia Gravis—DR Restriction of Autoimmune T Epitopes and Binding of Synthetic Receptor Sequences to DR Molecules," *J. Immunol.*, 152, 4165–4174 (1994).

Moskaug, J. O., et al., "Translocation of Diphtheria Toxin A–Fragment to the Cytosol—Role of the Site of Intrafragment Cleavage," *J. Biol. Chem.*, 264, 15709–15713 (1989).

Panina–Bordignon, P., et al., "Universally Immunogenic T. Cell Epitopes: Promiscuous Binding to Human MHC Class II and Promiscuous Recognition by T Cells," *Eur. J. Immunol.*, 19, 2237–2242 (1989).

Protti, M. P., et al., "Myasthenia Gravis: Recognition of a Human Autoantigen at the Molecular Level," *Immunol. Today*, 14, 363–368 (1993).

Ramakrishnan, et al., "Cytotoxic Conjugates Containing Translational Inhibitory Proteins," *Ann. Rev. Pharmacol. Toxicol.*, 32, 579–621 (1992).

Reece, J. C., "Mapping the Major Human T Helper Epitopes of Tetnus Toxin—The Emerging Picture," *J. Immunol.*, 151, 6175–6184 (1993).

Scheilbel, I., et al., "Immunization of Adults Against Diphtheria," *Acta Pathol. et Microbiol. Scand.*, 27, 69–77 (1950).

Siegall, C. B., "Targeted Toxins as Anticancer Agents," *Cancer*, 74, 1006–1012 (1994).

Vitetta et al., "Immunotoxins: Magic Bullets or Misguided Missiles," *Trends Pharmacol. Sci.*, 14, 148–154 (1993).

```
  1 GADDVVDSSKSFVMENFSSYHGTKPGYVDSIQKGIQKPKSGTQGNYDDDW
 51 KGFYSTDNKYDAAGYSVDNENPLSGKAGGVVKVTYPGLTKVLALKVDNAE
101 TIKKELGLSLTEPLMEQVGTEEFIKRFGDGASRVVLSLPFAEGSSSVEYI
151 NNWEQAKALSVELEINFETRGKRGQDAMYEYMAQACAGNRVRRSVGSSLS
201 CINLDWDVIRDKTKTKIESLKEHGPIKNKMSESPNKTVSEEKAKQYLEEF
251 HQTALEHPELSELKTVTGTNPVFAGANYAAWAVNVAQVIDSETADNLEKT
301 TAALSILPGIGSVMGIADGAVHHNTEEIVAQSIALSSLMVAQAIPLVGEL
351 VDIGFAAYNFVESIINLFQVVHNSYNRPAYSPGHKTQPFLHDGYAVSWNT
401 VEDSIIRTGFQGESGHDIKITAENTPLPIAGVLLPTIPGKLDVNKSKTHI
451 SVNGRKIRMRCRAIDGDVTFCRPKSPVYVGNGVHANLHVAFHRSSSEKIH
501 SNEISSDSIGVLGYQKTVDHTKVNSKLSLFFEIKS
```

FIG. 1A (PRIOR ART)

```
  1 GADDVVDSSKSFVMENFSSYHGTKPGYVDSIQKGIQKPKSGTQGNYDDDW
 51 KGFYSTDNKYDAAGYSVDNENPLSGKAGGVVKVTYPGLTKVLALKVDNAE
101 TIKKELGLSLTEPLMEQVGTEEFIKRFGDGASRVVLSLPFAEGSSSVEYI
151 NNWEQAKALSVELEINFETRGKRGQDAMYEYMAQACAGNRVRRSVGSSLS
201 CINLDWDVIRDKTKTKIESLKEHGPIKNKMSESPNKTVSEEKAKQYLEEF
                                      271-290
251 HQTALEHPELSELKIVIGTNPVFAGANYAAVNVAQVIDSETADNLEKT
                                      331-350
                321-340
301 IAALSILPGIGSVMGIADGAVHHNTEEIVAQSIALSSLMVAQAIPLYGEL
    351-370
351 VDIGFAAVNFVESIINLEQVVHNSYNRPAYSPGHKTQPFLHDGYAVSWNT
           411-430                  431-450
401 VEDSIIRTGFQGESGHDIKITAENTPLPLAGVLLPLTIPGKLDVNKSKTHI
451 SVNGRKIRMRCRAIDGDVTFCRPKSPVYVGNGVHANLHVAFHRSSSEKIH
501 SNEISSDSIGVLGYQKTVDHTKVNSKLSLFFEIKS
```

FIG. 1B

| DR allele | | | | | | Motif position | | | | | | | | | | |
|---|---|---|---|---|---|---|---|---|---|---|---|---|---|---|---|---|
| | | | | | | 1 | 2 | 3 | 4 | 5 | 6 | 7 | 8 | 9 | | |
| DRB1 0101 | | | | V | Q | P | F | A | G | A | N | Y | A | A | A | V | N | V | A | Q | V | I |
| | | | | H | N | I | L | S | S | N | M | A | A | Q | A | I | P | L | G | E | I | D |
| | | | | H | | T | I | V | A | L | I | G | L | S | S | L | M | E | L | H | | |
| | D | | | I | G | E | L | P | T | I | P | S | K | L | D | V | K | S | K | T | | |
| | V | | | G | F | V | Y | N | F | V | E | I | H | N | V | F | Q | V | T | H | | |
| | | | | | | | | | | | | | I | | | | | | | I | | |
| DRB1 0401 | | | | V | | P | F | A | G | A | N | Y | A | A | A | A | N | V | A | Q | V | I |
| | | Q | | D | I | A | L | S | L | M | M | V | Q | I | I | I | L | V | V | E | L | D |
| | V | I | | S | A | A | Y | S | V | E | E | E | L | P | P | F | Q | G | | | | |
| | D | G | | E | A | K | H | N | A | N | T | S | A | L | A | | | | | | | |
| | S | H | | S | D | | L | F | | K | | I | E | H | | | | | | | | |
| | G | I | | G | I | | | | | | | S | N | | | | | | | | | |
| | E | P | | H | K | | | | | | | | T | | | | | | | | | |
| DRB1 0402 | | | | | Q | | P | F | A | A | L | I | N | Y | A | A | A | A | V | N | V | A | Q | V | I |
| | V | | | A | A | I | L | S | S | A | M | H | V | A | Q | A | I | P | L | V | G | I | D |
| | D | | | Q | Y | H | V | E | G | S | H | I | T | L | L | E | V | E | V | V | E | A | |
| | I | | | G | N | H | H | S | F | S | I | H | K | A | F | N | N | N | | | L | | |
| | G | | | E | K | I | | D | A | H | K | K | S | E | Q | T | T | T | | | | | |
| | F | | | S | P | P | | I | E | D | | | | N | H | P | P | H | | | | | |
| | | G | | T | | | | | | | | | | T | | L | L | I | | | | | |
| | | | | I | | | | | | | | | | H | | A | I | A | | | | | |
| DRB1 0404 | | | | | | V | P | F | A | N | Q | I | N | A | A | A | A | V | N | V | A | Q | V | |
| | | Q | | | H | D | L | V | Q | I | S | M | V | L | L | L | S | L | A | V | G | L | F |
| | V | G | | N | I | I | I | S | L | A | M | A | A | S | Q | S | N | M | L | V | E | A | Q |
| | D | E | | T | D | K | H | G | E | E | A | Y | T | N | N | A | F | P | G | E | L | | |
| | I | S | | E | V | | L | F | | N | | Y | S | Y | F | I | V | L | I | L | P | | |
| | G | G | | Q | K | | | T | | K | | | | A | V | P | E | I | H | P | I | | |
| | F | H | | | | | | D | | S | | | | L | E | F | S | A | | I | A | | |
| | | I | | | | | | | | | | | | S | | V | | | | A | | | |
| | | P | | | | | | | | | | | | | | E | | | | | | | |

FIG. 6

DIPHTHERIA TOXIN EPITOPES

STATEMENT OF GOVERNMENT RIGHTS

The present invention was made with the support of the United States Government via a grant from NINCDS (Grant No. NS 23919). The government has certain rights in the invention.

BACKGROUND OF THE INVENTION

Diphtheria toxin (DTX) is a catalytic protein secreted by *Corynebacterium diphtheriae*, the causative agent of diphtheria (Collier et al., *Bacteriol. Rev.*, 39, 54 (1975)). This protein is a potent exotoxin that is transported in the blood of an infected organism to remote tissues, causing hemorrhagic and necrotic damage to those tissues in susceptible organisms. DTX is a single chain of 535 amino acids (Greenfield et al., *PNAS USA*, 80, 6853 (1983)), (SEQ ID NO:1) which, upon mild trypsinization and reduction in vitro breaks into fragments A (21 kDa) (SEQ ID NO:8) and B (37 kDa) (SEQ ID NO:9) (Collier et al., *J. Biol. Chem.*, 246, 1496 (1971); Moskaug et al., *J. Biol. Chem.*, 264, 15709 (1989)).

In the cytoplasm, the A fragment catalyses ADP-ribosylation of a translationally modified histidine residue (diphthamide) on elongation factor-2, leading to the arrest of protein synthesis (Collier et al., In: *ADP Ribosylation Reactions: Biology and Medicine*, Academic Press, Inc., New York, p. 573 (1982)). While DTX is quite immunogenic, only anti-DTX IgG can inactivate the biologic activity of DTX. Inactivation depends on the antibody having a greater affinity for the toxin than the toxin has for its substrate. Thus, only high affinity hyperimmune IgG can achieve anti-toxin activity. The production of high affinity IgG requires, in the vast majority of cases, and specifically in the case of DTX, interaction of B cells with antigen-specific T helper (CD4$^+$) cells.

Because diphtheria mortality is due to the effects of DTX, the key component of anti-diphtheria vaccines is diphtheria toxoid (DTD), a partially denatured, non-toxic form of DTX. Mass vaccination against diphtheria is carried out in virtually every country and entails several injections of vaccine to establish a good level of immunity, followed by periodic boosts at 10 or more years apart, during adult life.

While the existing anti-diphtheria vaccine preparations contain substantial amounts of bacterial impurities, they are highly effective in inducing high affinity antibody titers. However, these vaccines cause substantial undesirable side effects in a high percentage of immunized individuals. Severe side effects include convulsions (1/1750 doses), collapse (1/1750 doses), and acute encephalopathy (1/110,000 doses) which can result in permanent neurological damage. Less serious side effects include fever, pain, swelling and inconsolable crying in 10–15% of immunized children.

10–14% of adults also experience side effects, again ranging from mild to severe, primarily the result of sensitization to Corynebacterium proteins or toxin, or other corynebacteria. The majority of severe reactions in adults correlates with the administration of the standard dose of the vaccine, i.e., 12 units (Scheibel et al., *Acta Pathol. et Microbiol. Scand.*, 27, 69 (1950)). Such severe reactions can be reduced when a smaller dose, e.g., 1 unit, is used, however, a protective antibody response with the lower dose vaccine is only obtained when multiple immunizations are employed. Such a vaccination protocol is frequently unsuccessful due to low compliance of healthy subjects. This low compliance and the decrease over time of protective antibody response after immunization has led to a resurgence in cases of diphtheria in adults.

For unimmunized adults, passive immunotherapy with diphtheria anti-toxin is the only specific and effective treatment. However, commercial preparations of anti-toxin are derived from immunized non-human mammals, thus, providing a risk of inducing sensitization or anaphylactic reactions when these preparations are used.

Studies using synthetic sequences of protein antigens (Ags), such as the muscle nicotinic acetylcholine receptor (AChR), the autoAg in myasthenia gravis, and tetanus toxin (TTX), have identified epitopes recognized by human T-helper (Th or CD4$^+$) cells (Protti et al., *Immunol. Today*, 14, 363 (1993); Demoiz et al., *J. Immunol.*, 142, 394 (1989); Reece et al., *J. Immunol.*, 151, 6175 (1993)). Moreover, studies with AChR and TTX demonstrated that some sequence regions in these Ags comprise epitope(s) recognized by CD4$^+$ cells in many or all of the subjects tested, irrespective of their HLA class II haplotype (Protti et al., *Immunol. Today*, 14, 363 (1993); Panina-Bordingnon et al., *Eur. J. Immunol.* 19, 2237 (1989)). A sequence which is recognized by CD4$^+$ cells irrespective of their HLA class II haplotype is termed an Immunodominant Region Sequence, or "IRS."

Thus, what is needed is a method to identify an IRS in DTX.

SUMMARY OF THE INVENTION

The present invention provides six synthetic peptides consisting essentially of the following amino acid sequences:

(1) Pro-Val-Phe-Ala-Gly-Ala-Asn-Tyr-Ala-Ala-Trp-Ala-Val-Asn-Val-Ala-Gln-Val-Ile-Asp (SEQ ID NO:2);

(2) Val-His-His-Asn-Thr-Glu-Glu-Ile-Val-Ala-Gln-Ser-Ile-Ala-Leu-Ser-Ser-Leu-Met-Val (SEQ ID NO:3);

(3) Gln-Ser-Ile-Ala-Leu-Ser-Ser-Leu-Met-Val-Ala-Gln-Ala-Ile-Pro-Leu-Val-Gly-Glu-Leu (SEQ ID NO:4);

(4) Val-Asp-Ile-Gly-Phe-Ala-Ala-Tyr-Asn-Phe-Val-Glu-Ser-Ile-Ile-Asn-Leu-Phe-Gln-Val-Val (SEQ ID NO:5);

(5) Gln-Gly-Glu-Ser-Gly-His-Asp-Ile-Lys-Ile-Thr-Ala-Glu-Asn-Thr-Pro-Leu-Pro-Ile-Ala (SEQ ID NO:6); and (6) Gly-Val-Leu-Leu-Pro-Thr-Ile-Pro-Gly-Lys-Leu-Asp-Val-Asn-Lys-Ser-Lys-Thr-His-Ile (SEQ ID NO:7).

These peptides are depicted conventionally, from the amino terminus (left end) to the carboxyl terminus (right end), and formally represent amino acid residues 271–290 (SEQ ID NO:2); 321–340 (SEQ ID NO:3); 331–350 (SEQ ID NO:4); 351–370 (SEQ ID NO:5); 411–430 (SEQ ID NO:6); and 431–450 (SEQ ID NO:7) of the diphtheria toxin secreted by *Corynebacterium diphtheriae* (SEQ ID NO:1, Greenfield et al., *PNAS USA*, 80, 6853 (1993)).

These peptides each can stimulate the proliferation of anti-diphtheria toxoid (DTD) CD4$^+$ T cell lines or anti-DTD PBMC from many, or all, individuals, irrespective of the HLA-haplotype of the individual, as determined by the proliferation assays described hereinbelow. These peptides can be prepared in large quantities and in high purity by chemical syntheses and thus are much less expensive and more readily obtained than a pure DTX-derived antigen.

T cell epitopes can vary in size, and a portion of the claimed peptides, as small as seven consecutive amino acid residues, may stimulate the proliferation of anti-DTD or anti-DTX CD4$^+$ cells. Thus, immunogenic fragments or subunits of the claimed peptides are also within the scope of the present invention.

Identification of an IRS can facilitate the design of peptide-based or peptide-enhanced vaccines for immunoprophylaxis of diphtheria. Furthermore, immunoconjugates of DTX have been used for targeted killing of cells, such as cancerous and HIV-infected cells (Vitetta et al., *Trends Pharmacol. Sci.,* 14, 148 (1993); Siegall, *Cancer,* 74, 1006 (1994); Ramakrshran et al., *Ann. Rev. Pharmacol. Toxicol.,* 32, 579 (1992)). Most CD4$^+$ epitopes are within fragment B of DTX, as described below, while fragment A, which bears the toxic catalytic domain and is the active part of DTX immunoconjugates, is poorly recognized by CD4$^+$ cells. Therefore, better DTX immunotoxins and hormonotoxins should contain fragment A only, thus minimizing undesirable CD4$^+$ responses and optimizing the long-term efficacy of the conjugate.

Another embodiment of the invention is an isolated and purified peptide consisting essentially of an amino acid sequence homologous or identical to a portion of the diphtheria toxin amino acid sequence. The peptide can be between 7 and 40 amino acid residues in length. A portion of the amino acid sequence in the peptide contains a contiguous sequence of amino acid residues that form at least one alpha helix or a beta sheet in vitro or in vivo. Preferably, the isolated peptide comprises an immunodominant region sequence.

Yet another embodiment of the invention is an essentially pure population of human T-helper (Th) cells having a receptor site for at least one synthetic diphtheria toxin-specific peptide which peptide comprises a immunodominant region sequence.

Also provided is a method to identify an immunogenic epitope. The method comprises exposing cultured peripheral blood mononuclear cells to at least one isolated and purified peptide, wherein the amino acid sequence of the peptide is homologous or identical to a portion of the amino acid sequence of diphtheria toxin. Then it is determined whether or not the cultured peripheral blood mononuclear cells proliferate relative to control peripheral blood mononuclear cells which were not exposed to the peptide or any other antigenic stimulus.

Also provided is a method to identify an immunodominant region sequence in a diphtheria toxin peptide. This method comprises exposing each of at least a first and a second culture of peripheral blood mononuclear cells to at least one isolated and purified peptide, wherein the HLA haplotype of the peripheral blood mononuclear cells in at least the first and second of the cultures is different, and wherein the amino acid sequence of the peptide is homologous or identical to a portion of the amino acid sequence of diphtheria toxin. Then it is determined whether or not the peripheral blood mononuclear cells in any of the exposed cultures proliferates relative to control peripheral blood mononuclear cells which were not exposed to the peptide or any other antigenic stimulus. A preferred embodiment of the invention employs peripheral blood mononuclear cells which were previously stimulated in vitro. A more preferred embodiment of the invention employs peripheral blood mononuclear cells previously stimulated with diphtheria toxoid, diphtheria toxin, or diphtheria toxin-specific peptides to yield CD4$^+$ T cell lines which are specific for diphtheria toxin epitopes or highly enriched in CD4$^+$ cells specific for diphtheria toxin epitopes.

Yet another embodiment of the invention is a vaccine. The vaccine comprises an immunogenic amount of at least one DTX-specific peptide containing an immunodominant region sequence. The peptide is combined with a physiologically acceptable, non-toxic liquid vehicle, optionally comprising conventional vaccine adjuvants. The amount of peptide administered is effective to immunize a susceptible mammal against *Corynebacterium diphtheriae.* A preferred embodiment of the invention employs a vaccine which further comprises diphtheria toxoid.

Also provided is an immunogenic composition. The composition comprises a peptide coupled to a non- or poorly immunogenic molecule. The peptide consists essentially of an amino acid sequence homologous or identical to a portion of the diphtheria toxin amino acid sequence. The peptide is between 7 and 40 amino acid residues in length and a portion of the amino acid sequence in the peptide contains a contiguous sequence of amino acid residues that form at least one alpha helix or a beta sheet in vitro or in vivo.

Another embodiment of the invention is an immunogenic composition which comprises a peptide coupled to a non- or poorly immunogenic molecule. The peptide consists essentially of an amino acid sequence region that is present on the surface of crystallized diphtheria toxin.

Yet a further embodiment of the invention is a method to identify an immunogenic epitope. The method comprises exposing cultured peripheral blood mononuclear cells to at least one isolated and purified peptide, wherein the amino acid sequence of the peptide is homologous or identical to a portion of the amino acid sequence of diphtheria toxin. Then it is determined whether or not the cultured peripheral blood mononuclear cells produce at least one interleukin relative to control peripheral blood mononuclear cells which were not exposed to the peptide or any other antigenic stimulus.

Also provided is a method to identify an immunodominant region sequence in a diphtheria toxin peptide. The method comprises exposing each of at least a first and a second culture of peripheral blood mononuclear cells to at least one isolated and purified peptide, wherein the HLA haplotype of the peripheral blood mononuclear cells in at least the first and second of the cultures is different, and wherein the amino acid sequence of the peptide is homologous or identical to a portion of the amino acid sequence of diphtheria toxin. Then it is determined whether or not the peripheral blood mononuclear cells in any of the exposed cultures produce at least one interleukin relative to control peripheral blood mononuclear cells which were not exposed to the peptide or any other antigenic stimulus.

Also provided are an immunotoxin consisting essentially of fragment (SEQ ID NO:8) of diphtheria toxin linked to a binding protein that can specifically bind to a particular cell population, wherein the binding protein is an antibody molecule or a portion thereof with binding activity, and a hormonotoxin consisting essentially of fragment A of diphtheria toxin linked to a binding protein that can specifically bind to a particular cell population, wherein the binding protein is a hormone molecule or a portion thereof with binding activity.

As used herein, the term "immunogenic" with respect to an agent, such as a peptide, means that the agent can induce peripheral blood mononuclear cells (PBMC) or other lymphoid cells to proliferate when those cells are exposed to the agent, relative to cells not exposed to the agent.

As used herein, "immunodominant epitope" or "immunodominant domain" is an amino acid sequence containing the smallest number of contiguous amino acid residues necessary and sufficient to induce the proliferation of a CD4$^+$ cell regardless of the HLA class II haplotype of that cell.

As used herein, the term "immunodominant" region sequence, or "IRS," is an amino acid sequence which contains at least one immunodominant epitope as well as other sequences which do not contribute to a immunodominant epitope. The IRS induces the proliferation of a CD4+ cell regardless of the HLA class II haplotype of that cell. Sequences which do not contribute to the IRS can be present at either or both the amino- or carboxyl- terminal end of the IRS.

As used herein, the term "consisting essentially of" with respect to a claimed peptide sequence is defined to mean that at least a majority, i.e., 51%, of the amino acid sequence of the peptide comprises an IRS. The non-IRS sequences preferably are no more than about 10–20 peptidyl residues in toto, and either do not affect the immunogenic activity of the peptide or do not reduce the activity by more than 10–20%.

As used herein, the term "consisting essentially of" with respect to an immuno- or hormono-toxin is defined to mean that the immuno- or hormono-toxin can contain, in addition to fragment (SEQ ID NO:8) of diphtheria toxin coupled or linked to an antibody or hormone molecule, or a portion thereof which confers binding activity, other agents which do not reduce or impair either the binding or toxin activity of the immuno-or hormono-toxin.

As used herein, the term "CD8+ depleted" or "CD4+ enriched" with respect to a cell population, means that after depletion, the population has fewer CD8+ cells than prior to depletion and/or contains at least about 40–60% of the total number of cells present prior to depletion.

As used herein, the term "homologous" with respect to a diphtheria toxin-specific peptide or protein sequence means that the amino acid sequence has at least 80%, preferably at least 90%, identity with SEQ ID NO:1.

BRIEF DESCRIPTION OF THE FIGURES

FIG. 1. Position of synthetic DTX specific peptides relative to the sequence of DTX (SEQ ID NO:1, Greenfield et al., *PNAS USA*, 80, 6853 (1993)). Synthetic peptides which comprise an IRS are indicated by a numerical code which includes two numbers. The first number refers to the position of the first residue in the peptide on the DTX sequence, and the second number refers to the last residue in the peptide on the DTX sequence. The uncharged DTX sequence regions identified by Sette et al. (*J. Immunol.*, 151, 3163 (1993)) are indicated by blackened boxes.

FIG. 6. DTX synthetic sequences containing an IRS (SEQ ID NOS:2–7). The IRSs were aligned according to binding motifs identified for the DRB1 0101, 0401, 0402, and 0404 alleles. Residues in boxes conform to the motifs proposed by Hammer et al. (*Cell*, 74, 197 (1993)), Hammer et al. (*J. Exp. Med.*, 176, 1007 (1995)), Hammer et al. (*J. Exp. Med.*, 181, 1847 (1995)), Hammer et al. (*PNAS USA*, 91, 4456 (1994)), and Sette et al. (*J. Immunol.*, 151, 3163 (1993)).

DETAILED DESCRIPTION OF THE INVENTION

Figure 2:
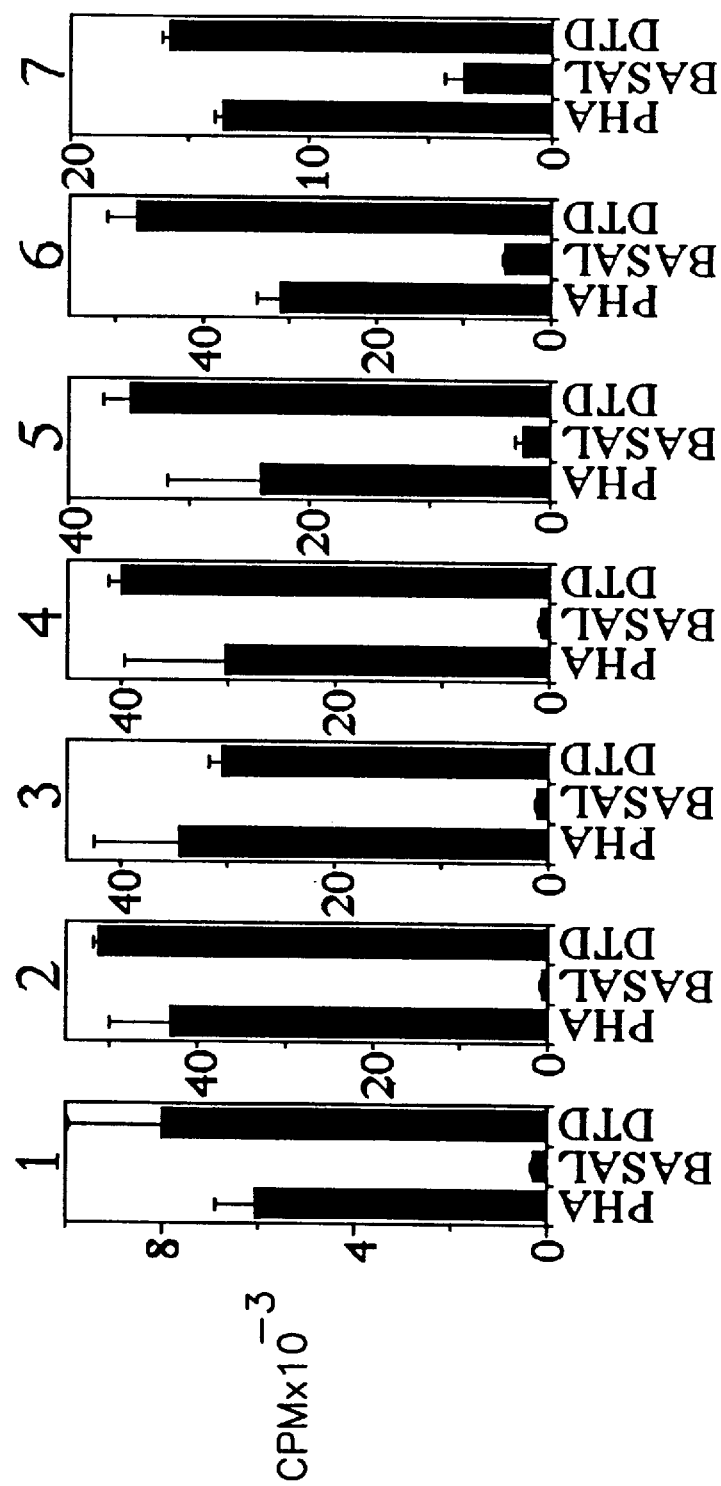
FIG. 2. Response of CD4+ lines to PHA and DTD. CD4+ lines (Table 2) were isolated by subjecting PBMC from seven healthy individuals to repeated cycles of DTD stimulation. The lines were then challenged in proliferation assays with either 10 µg/ml of phytohemagglutinin (PHA) or 10 µg/ml of DTD. The bars represent the average±SD of triplicate cultures. The basal rate of cell proliferation of the lines in the presence of antigen presenting cells (APC) but in the absence of the antigen ("Basal") is shown, but was not subtracted from the response to PHA or DTD. The stimulation scale, i.e., cpm, is different for different lines.
Figure 3A:
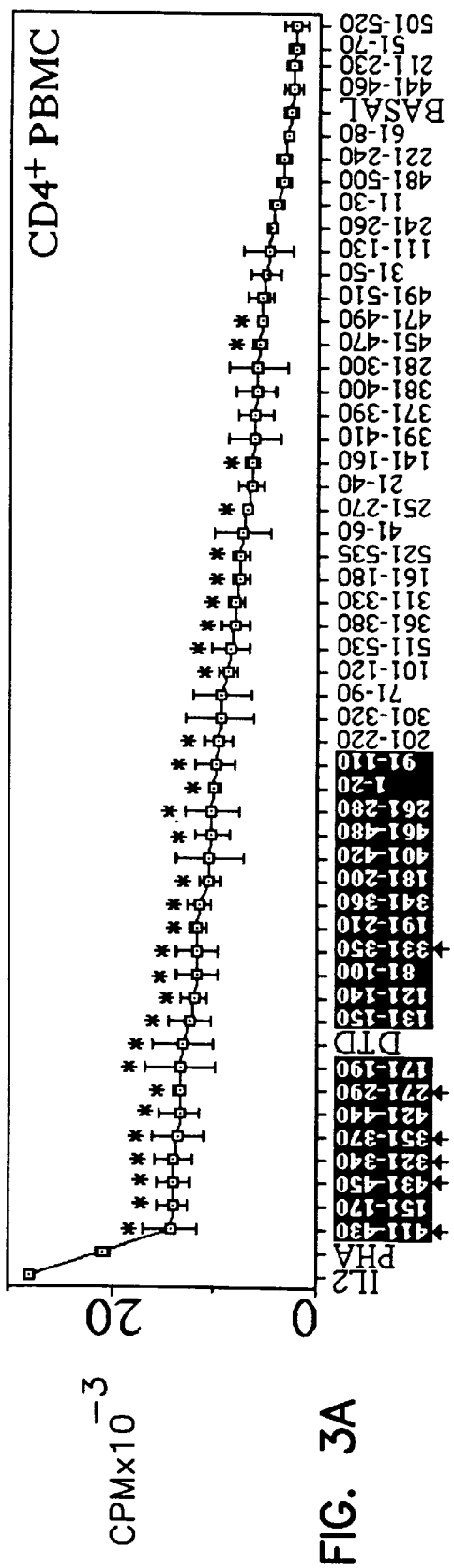
FIG. 3. Recognition of synthetic DTX sequences by CD4+ enriched PBMC and anti-DTD cell lines derived from the same subject. CD4+ enriched PBMC or an anti-DTD CD4+ cell line derived from subject #4 were challenged in a proliferation assay with individual DTX synthetic sequences (10 µg/ml), as indicated along the abscissa. Proliferation assays were also conducted in the presence of IL-2 (10%), PHA (10 µg/ml), or DTD (10 µg/ml). Basal rates of proliferation were assessed by culturing CD4+ enriched PBMC or CD4+ cell lines plus APC without any stimulus ("Basal"). These basal rates were not subtracted from the rates observed in the presence of antigen (Ag). Data are averages±SD of triplicate cultures, and they are arranged in order of decreasing intensity of response. IRS peptides are indicated by arrows. In the top panel, the peptides that induced a significant ($p<0.01$) response of the CD4+ enriched PBMC are indicated with an asterisk (*).
Figure 3B:
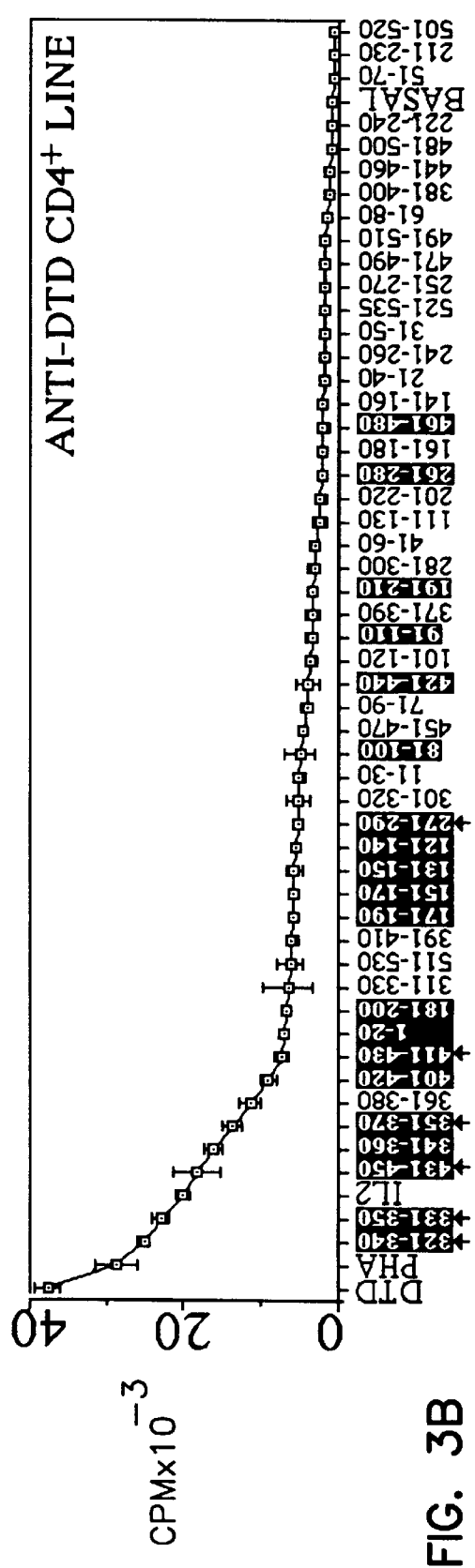
Figure 4:
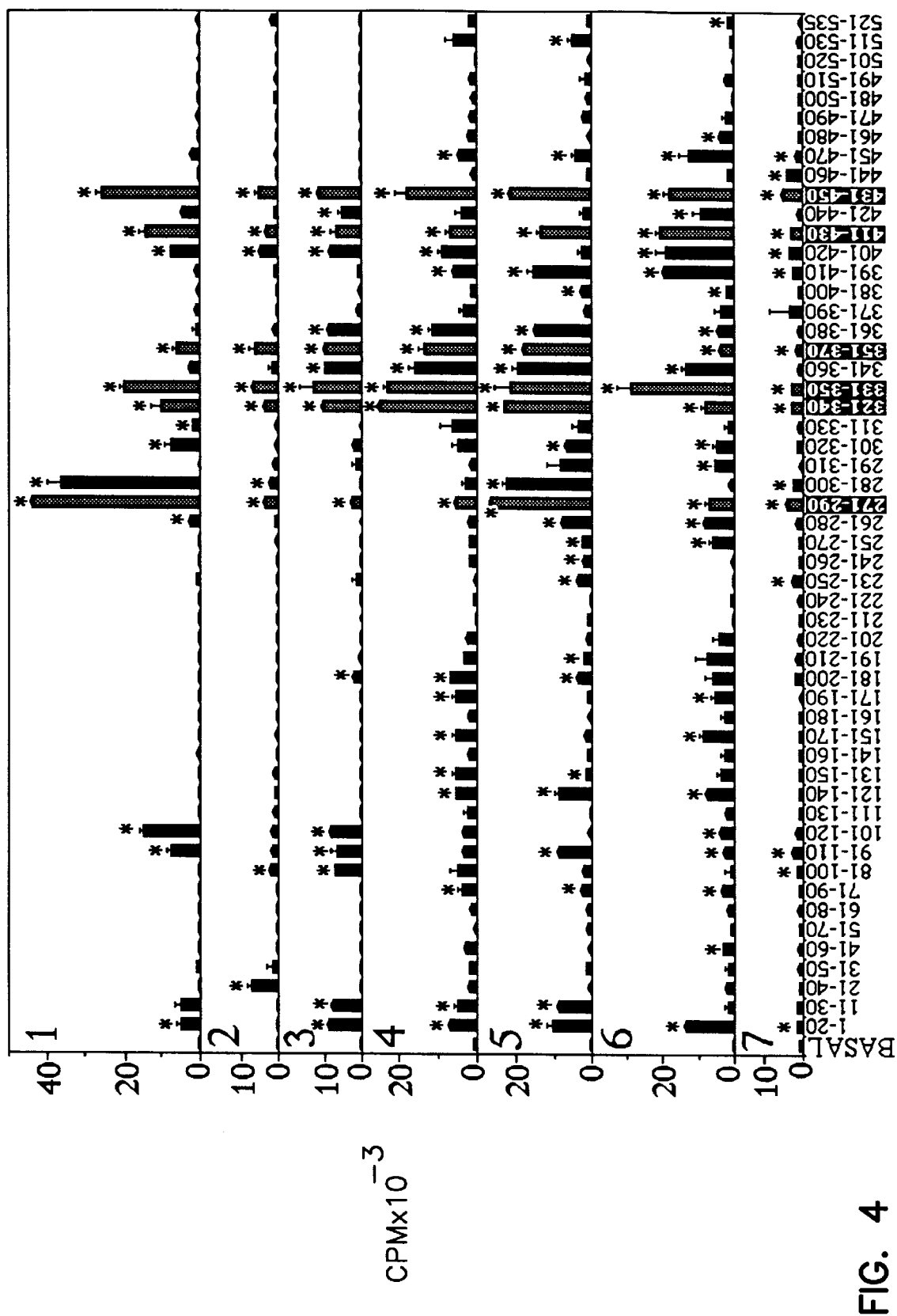
FIG. 4. Synthetic peptides of DTX recognized by anti-DTD CD4+ cell lines. CD4+ cell lines from the seven subjects were challenged in proliferation assays with individual synthetic DTX peptides, as indicated along the abscissa. The bars represent average±SD of triplicate cultures. The basal rate of cell proliferation, in the absence of the antigenic stimulus but in the presence of APC, is reported ("basal"). The basal rate was not subtracted from the response to the peptides. Asterisks (*) above the bars represent significant ($p<0.005$) responses, as assessed by a two-tailed student's t test. Although each subject had an individual pattern of peptide recognition, six peptides, indicated by checkered boxes, were recognized by all subjects.
Figure 5A:
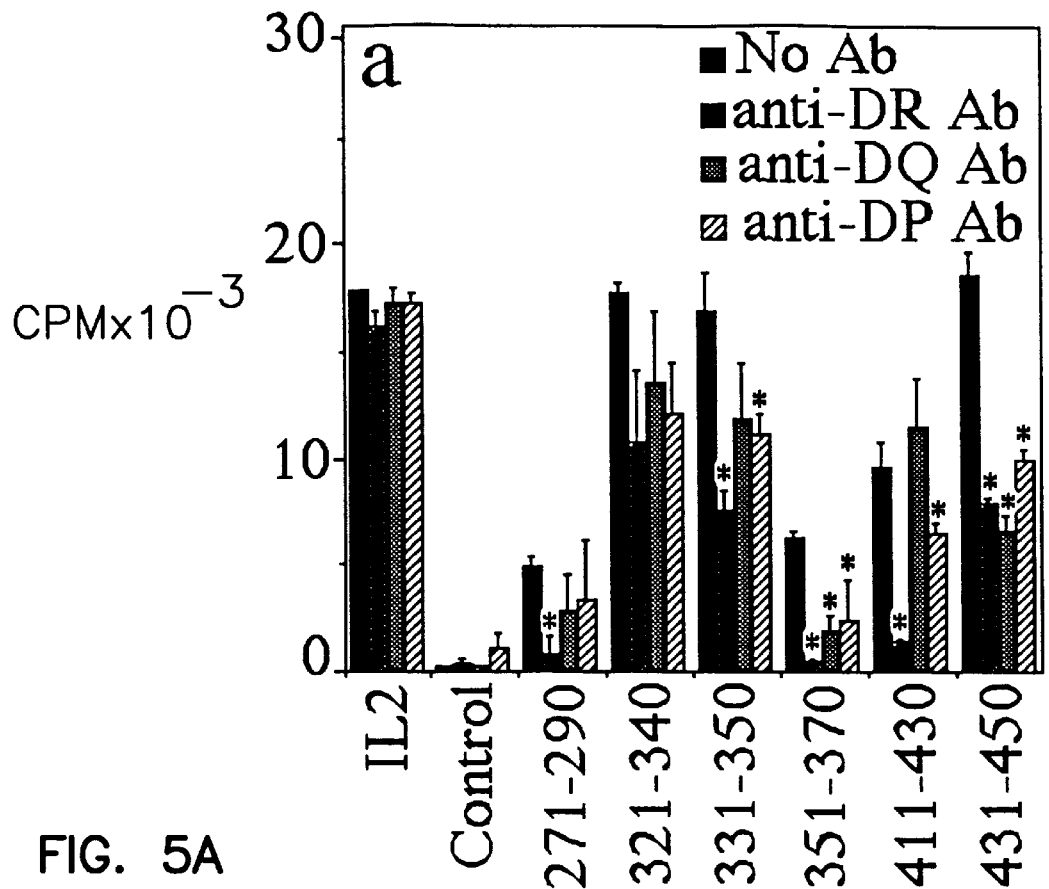
FIG. 5. HLA class II restriction of DTX IRSs in two subjects. Anti-DTD CD4+ lines from subject #3 (panel a) and subject #1 (panel b) were challenged in a proliferation assay with IL-2 (10%), a 20-residue synthetic sequence unrelated to DTX (SEQ ID NO:61, 10 µg/ml, "Control"), or individual IRS containing peptides (SEQ ID NOS:2–7), as indicated along the abscissa. The bars represent average±SD of triplicate cultures. The proliferation assays were carried out in the absence of anti-class II monoclonal antibody (mAb, black bars), or in the presence of mAb against DR, DQ, or DP molecules, as indicated. Asterisks (*) represent a significant ($p<0.05$) decrease in the response to the peptide when the mAb was present, as compared to the response in the absence of the mAb.
Figure 5B:
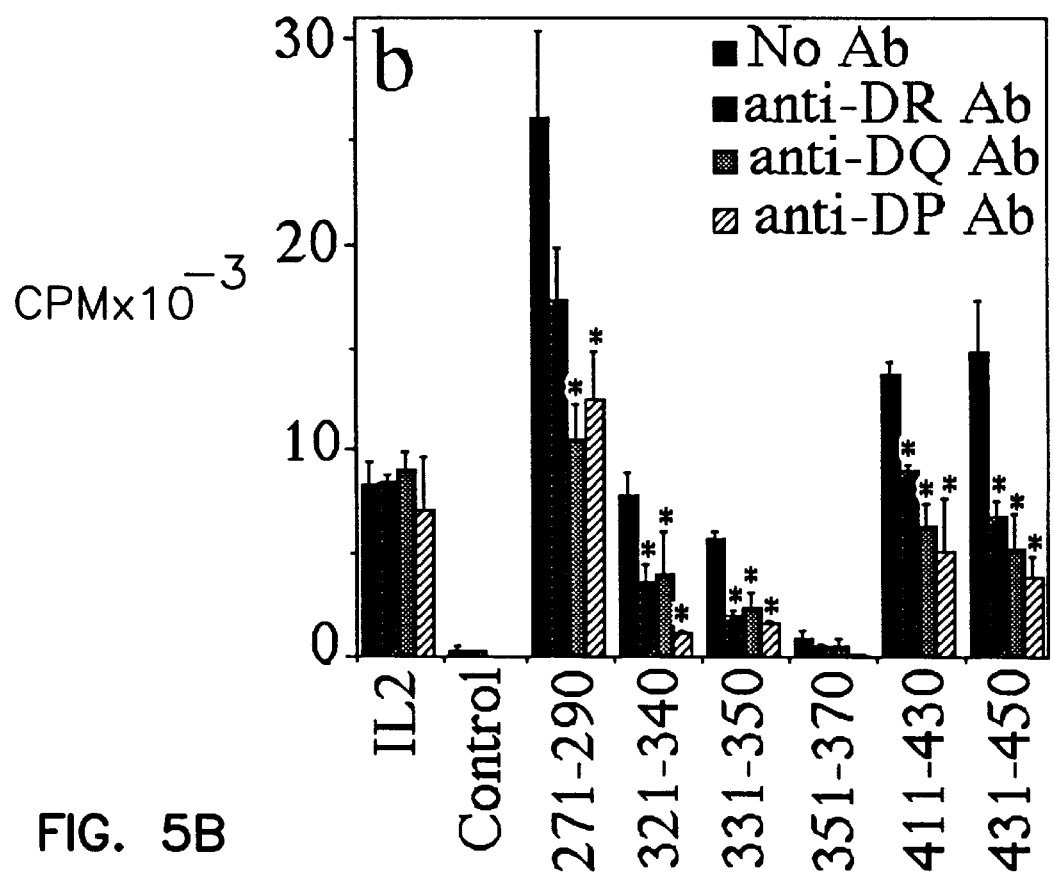

DTX is a good antigen to use to study immune recognition in humans, because most individuals are immunized against this antigen, and the three dimensional structure of DTX is known (Chol et al., *Nature*, 357, 216 (1992); Bennett et al., *Protein Sci.*, 3 (1994); Bennett et al., *Protein Sci.*, 3, 1464 (1994)). As discussed above, existing anti-diphtheria vaccines frequently produce undesirable side effects of differing severity, especially in adults. While these side effects are reduced when a low dose is used, a single low dose is not effective in inducing protective antibody titers.

The identification of an IRS in DTX, described hereinbelow, permits the development and use of a peptide-based or peptide-enhanced vaccine to DTX. DTX-specific peptides which contain an IRS can induce an immune response in many, if not all, individuals, regardless of HLA haplotype. Moreover, such vaccines will not produce the undesirable side effects associated with the contaminants present in the anti-diphtheria vaccines currently in use because the vaccines lack material currently employed in diphtheria vaccines, i.e., they are peptide-based vaccines, or only contain these materials in low amounts, i.e., they are peptide-enhanced vaccines. Thus, at least one DTX-specific peptide containing an IRS, where the peptide is of sufficient length to induce a B cell response, can be administered as the active component of an anti-DTX vaccine. A more preferred embodiment of the invention is the administration of a vaccine comprising a plurality of DTX-specific peptides each containing an IRS, wherein each peptide is of sufficient length to trigger a B cell response.

To prepare the vaccine, peptides would be synthesized or otherwise obtained and then lyophilized and stabilized. The peptide can then be adjusted to the appropriate concentration, and optionally combined with other agents. The absolute weight of a given peptide included in a unit dose of a vaccine can vary widely. For example, 0.5–10 mg, preferably 1–5 mg, of at least one DTX-specific peptide, and preferably a plurality of DTX-specific peptides, containing an IRS, can be administered. The dose administered can depend upon factors such as the weight, age, and physical condition of the mammal to be immunized. Such factors can be readily determined by the clinician employing animal models or other test systems which are well known to the art. A unit dose of the vaccine is preferably administered parenterally, e.g., by subcutaneous or by intramuscular injection.

A preferred embodiment of the invention is an enhanced DTX-specific peptide-based vaccine which comprises at least one DTX-specific peptide containing an IRS and an amount of DTD which is sufficient to induce an antibody response. Administration of synthetic peptides of a given protein antigen containing $CD4^+$ T cell epitopes can potentiate the immune response to the antigen, i.e., DTD, given concomitantly or subsequently to the synthetic peptide epitope. Thus, the concomitant administration of a low dose of DTD with at least one DTX-specific peptide containing an IRS results in minimal undesirable side effects while stimulating both B and $CD4^+$ cells to produce an effective immune response. For example, such an enhanced peptide-based vaccine can include 1 unit of DTD plus 0.5–10 mg, preferably 1–5 mg, of at least one, preferably a plurality of, DTX-specific peptide containing an IRS. In infants, such a vaccine would follow the customary dosing schedule. In adults, a single dose of the enhanced vaccine may be needed every 3–5 years.

Either of these two embodiments produce a vaccine that is equally inexpensive and efficacious as the vaccines currently in use, but reduce or eliminate the side effects associated with the currently employed vaccines.

The Immune Response

The capacity to respond to immunologic stimuli resides primarily in the cells of the lymphoid system. During embryonic life, a stem cell develops, which differentiates along several different lines. For example, the stem cell may turn into a lymphoid stem cell which may differentiate to form at least two distinct lymphoid populations. One population, called T lymphocytes, is the effector agent in cell-mediated immunity, while the other, called B lymphocytes, is the primary effector of antibody-mediated, or humoral, immunity. The stimulus for B cell antibody production is the attachment of an Ag to B cell surface immunoglobulin. Thus, B cell populations are largely responsible for specific antibody production in the host. For most antigens, B cells require the cooperation of antigen-specific T helper ($CD4^+$) cells for effective production of high affinity antibodies.

Of the classes of T lymphocytes, T helper (Th) or $CD4^+$ cells are antigen-specific cells that are involved in primary immune recognition and host defense reactions against bacterial, viral, fungi and other antigens. $CD4^+$ cells are necessary to trigger high affinity IgG production from B cells for the vast majority of antigens, DTX being such an antigen. The T cytotoxic (Tc) cells are antigen-specific effector cells which can kill target cells following their infection by pathologic agents.

While $CD4^+$ cells are antigen-specific, they cannot recognize free antigen. For recognition and subsequent $CD4^+$ activation and proliferation to occur, the antigen must be processed by suitable cells (antigen presenting cells, APC). APC fragment the antigen molecule and associate the fragments with major histocompatibility complex (MHC) class II products present on the APC cell surface. These antigen fragments, or T cell epitopes, are thus presented to receptors or a receptor complex on the $CD4^+$ cell in association with MHC class II products. Thus, $CD4^+$ cell recognition of a pathogenic antigen is MHC class II restricted in that a given population of $CD4^+$ cells must be either autologous or share one or more MHC class II products with the APC. Likewise, Tc cells recognize Ag in association with MHC class I products.

In the case of $CD4^+$ cells, this antigen presenting function is performed by a limited number of APC. It is now well established that $CD4^+$ cells recognize peptides derived from processed soluble antigen in association with class II MHC product, expressed on the surface of macrophages. Recently, other cell types such as resting and activated B cells, dendritic cells, epidermal Langerhans' cells, and human dermal fibroblasts have also been shown to present antigen to $CD4^+$ T cells.

If a given $CD4^+$ cell possesses receptors or a receptor complex which enable it to recognize a given MHC class II product-antigen complex, it becomes activated, proliferates and generates lymphokines, such as interleukin 2 (IL-2). The lymphokines in turn cause the proliferation of several types of "killer" cells, including Tc cells and macrophages, which can exhibit antimicrobial and tumoricidal activity. After stimulation subsides, survivors of the expanded $CD4^+$ cells remain as member cells in the body, and can expand rapidly again when the same antigen is presented.

Numerous attempts have been made to isolate and maintain homogenous populations of Tc or $CD4^+$ cells and to characterize them in terms of their antigen specificity and MHC restriction. These attempts usually involve the stimulation of mononuclear cells from a seropositive human or murine host with antigenic bacterial or viral preparations in combination with non-proliferative APC, such as irradiated autologous mononuclear cells (MNC). Proliferating polyclonal populations of $CD4^+$ cells or Tc cells can be cloned by limiting dilution to obtain homogenous populations and then further proliferated and characterized by a variety of techniques.

Methods of determining whether PBMCs or lymphoid cells have proliferated, or produced or secreted interleukins, are well known in the art. For example, see Czerkinsky et al., *J. Immunol.*, 110, 29 (1988); Olsson et al., *J. Clin. Investig.*, 86, 981 (1990); Link et al., *J. Clin. Investig.*, 87, 2191 (1991).

The invention has been described with reference to various specific and preferred embodiments and will be further described by reference to the following detailed examples. It is understood however, that there are may extensive variations, and modifications on the basic theme of the present invention beyond that shown in the examples and description, which are within the spirit and scope of the present invention.

EXAMPLE

Overlapping synthetic peptides spanning the entire DTX sequence were employed to identify sequence regions recognized by CD4+ cells of seven healthy humans with different HLA haplotypes.

Materials and Methods

Subjects

Table 1 summarizes some salient features of the seven subjects studied. These patients had been immunized with DTD, and boosted either immediately prior to this study or in the recent past.

TABLE 1

| Subject # | Age, Sex | HLA-DR, DQ haplotype |
|---|---|---|
| 1. | 33, M | DR8(w8), DQw7(w3) |
| | | DR6(w14), DRw52c, DQw5(w1) |
| 2. | 44, F | DR5(w11), DRω52, DQw2 |
| | | DR4, DRω53, DQw7(w3) |
| 3. | 31, M | DR4, DRw53, DQw5(w1) |
| | | DR10(w10), DQw4 |
| 4. | 27, M | DR4(Dw10), DRω53, DQw8(w3) |
| | | DR2(w15), Dw2, DRω51, DQw6(w1) |
| 5. | 27, M | DR4, DRw53, DQw7(w3) |
| | | DR5(w12), DRw52a |
| 6. | 25, F | DR1, DQw5(w1) |
| | | DR2(w15), DRw51(Dw2), DQw6(w1) |
| 7. | 27, M | DR5(w12), DRw52c, DQw8(w3) |
| | | DR6(w13), DRw52, DQw6(w1) |

[a]Determined by restriction fragment length polymorphism (Noreen et al., Transp. Proc., 21, 2968 (1989)) and/or oligonucleotide typing (Kumura et al., In: Proceedings of the Eleventh International Histocompatibility Workshop and Conference: HLA, Oxford University Press, p. 397 (1992)).

Peptide synthesis 53 peptides, 20 residues long and overlapping each other by 10 residues were synthesized (SEQ ID NOS:2–7 and 10–56). In sum, the peptides corresponded to the complete DTX sequence (Houghton et al., PNAS USA, 82, 7048 (1988)). The length of the peptides was chosen because, although class II restricted epitopes are only 13–17 residues in length, the presence of extra residues does not interfere with epitope presentation, as the binding groove of DR molecules is open-ended on both sides (Stern et al., Nature, 368, 215 (1994)). The sequence overlap is close to the length of class II restricted T epitopes so as to reduce the chance of missing epitopes "broken" between peptides. Each peptide is numerically designated with a code which includes two numbers, referring to the position on the DTX sequence of the first and the last peptide residues.

The amino acid composition of the peptides found to contain IRSs was verified by phenylisothiocyanate derivatization of amino acid residues released by acid hydrolysis, followed by separation by reverse-phase HPLC (Heinrickson et al., Anal. Biochem., 136, 65 (1993)). The results of the composition analysis corresponded with the expected theoretical values. Consistent results were obtained for different batches of the same peptide sequence.

The molecular weight of peptides with IRSs was verified by mass spectrometry. For all peptides a major peak of the expected molecular weight was present.

CD8+ T cell depletion and proliferation assay

CD8+ T cells can inhibit the in vitro response of human CD4+ cells to Ags (Protti et al., J. Immunol., 144, 1276 (1990); Manfredi et al., J. Clin. Invest., 92, 1055 (1993)). Thus, the results of proliferation assays carried out with populations containing both CD4+ and CD8+ cells may be difficult to interpret. To identify a DTX peptide sequence recognized by CD4+ T cells in the peripheral blood, PBMC were depleted of CD8+ cells by paramagnetic beads. Yields of the CD8+ depleted, CD4+ enriched cell population (referred to as either CD4+ enriched or CD8+ depleted cells) were consistently 45–55% of the starting PBMC population.

CD4+ enriched cells, diluted to $1 \times 10^6$/ml in 1640 (Gibco, Grand Island, N.Y.) with 10% heat inactivated AB human serum, 2 mM L-glutamine, 100 U/ml penicillin and 50 μg/ml streptomycin (Tissue Culture Medium, TCM), were plated in triplicate in 96 round bottom well plates, and stimulated with each one of the following: phytohemagglutinin (PHA, 10 μg/ml, Wellcome, London, UK), interleukin 2 (IL-2, Lymphocult, Biotest Diagnostic Inc., Dreieich, Germany; final concentration of 10 U/ml), DTD (Wyeth Laboratories, Inc., Pennsylvania; 10 μg/ml), or an individual synthetic peptide. Basal growth rate was determined from triplicate wells containing CD4+ enriched cells cultivated without any stimulus. After five days, the cultures were pulsed for 16 hours with $^3$H-thymidine (1 μCi per well, specific activity 6.7 Ci/mmol, Amersham, Arlington Heights, Ill.), collected with a Titertek multiple harvester (Skatron Inc., Sterling, Va.), and the $^3$H-thymidine incorporation was measured by liquid scintillation.

Propagation of CD4+ cell lines specific for DTD and proliferation assay

PBMC were suspended ($1-2 \times 10^6$ cells/ml) in TCM containing 10 μg/ml DTD, and cultivated in T25 flasks (Costar, Cambridge, Mass.) for 1 week. The reactive lymphoblasts were isolated on Percoll gradients, expanded in TCM containing T-cell growth factor (TCGF, Lymphocult, Biotest Diagnostic, Dreieich, Germany, at a final concentration of IL-2 of 10 units/ml), and enriched in DTD-specific cells by weekly stimulations with the same amount of DTD plus irradiated (4,000 rads: 1 rad=0.01 Gy) autologous PBMC as APC. The response to DTD and PHA of the T cell lines obtained was tested weekly.

Proliferation assays with CD4+ cell lines for DTD

Proliferation assays were carried out with CD4+ lines, using $2 \times 10^4$ cells/well, irradiated autologous PBMC ($2 \times 10^5$ cells/well) as APC, and the Ags described above for CD4+ enriched PBMC. Basal growth rate (Blank) was determined from triplicate wells containing CD4+ cell lines cultivated without any stimulus. After one day, the cultured cells were pulsed for 16 hours with $^3$H-thymidine, collected, and the $^3$H-thymidine incorporation measured as described above for CD4+ enriched PBMC.

Flow cytometry

The phenotype of the T cell lines and of the CD4+ enriched PBMC was determined using a FACStar$^R$ cell sorter (Becton Dickinson and Co., Mountain View, Calif.) and phycoerythrin-conjugated Leu 4 (anti-CD3), and FITC-conjugated Leu 2 (anti-CD8) and Leu 3 (anti-CD4) antibodies (Becton Dickinson, San Jose, Calif.), as described by Mojola et al., J. Clin. Invest., 93, 1020 (1994)).

HLA class II restriction of CD4+ recognition of DTX IRSs

The DR, DP, or DQ restriction of the IRSs recognized by the anti-DTD CD4+ lines was investigated for all the lines in inhibition experiments, using commercially available purified anti-DR, anti-DP and anti-DQ mAbs (Becton Dickinson, San Jose, Calif.), as described by Mojola et al. (J. Immunol., 1521, 4686 (1994)).

Results

Propagation and characterization of anti-DTD T cell lines from healthy subjects

Anti-DTD T cell lines were successfully obtained from all the subjects tested. The lines were considered sufficiently enriched in anti-DTD T cells when their response to DTD in proliferation assays was comparable to, or better than, that of PHA. This occurred after 3–4 cycles of stimulation with DTD. The lines were predominantly or exclusively CD3+, CD4+, CD8– (Table 2). The results of one representative experiment for each line, testing the response to PHA and DTD, are shown in FIG. 2.

TABLE 2

| T cell line (Subject #) | CD3+ cells (%) | CD3+ CD4+ cells (%) | CD3+ CD8+ cells (%) |
| --- | --- | --- | --- |
| 1 | 91 | 84.3 | 0.8 |
| 2 | 94.7 | 78.2 | 4.5 |
| 3 | 98.3 | 89.3 | 2.1 |
| 4 | 96.9 | 80.2 | 5.8 |
| 5 | 96.8 | 90.7 | 0.5 |
| 6 | 92.8 | 82.3 | 0.7 |
| 7 | 95.6 | 88.6 | 3.2 |

Comparison of the recognition of synthetic DTX sequences by $CD4^+$ enriched PBMC and anti-DTD $CD4^+$ cell lines from the same subject Previous studies on the epitopes recognized by $CD4^+$ cells of normal subjects for TTX and of myasthenic patients for AChR, using unselected PBMC or $CD4^+$ enriched PBMC, found that the responses of unselected blood T cells were low and inconsistent (O'Sullivan et al., *J. Immunol.,* 147, 2663 (1991); Protti et al., *J. Immunol.,* 144, 1276 (1990); Manfredi et al., *J. Clin. Invest.,* 92, 1055 (1993); Manfredi et al., *Neurology,* 42, 1092 (1992)). This problem is circumvented by the use of Ag-specific $CD4^+$ lines propagated in vitro by stimulation with the relevant Ag.

Ag-specific lines have the important caveat that, due to biased clonal propagation in vitro, they might not be representative of the frequency of the starting clonal repertoire. Therefore, experiments were carried out comparing the responses to individual peptides of $CD4^+$ enriched PBMC and of anti-DTD $CD4^+$ lines from the same subject.

The anti-DTX $CD4^+$ lines propagated from subjects #4 and #5, and their $CD4^+$ enriched PBMC, were tested in proliferation assays with individual peptides. FIG. 3 illustrates the results obtained in one such comparative experiment, using subject #4. The $^3$H-thymidine incorporation obtained in response to DTD and to DTX-specific peptides was much higher for the $CD4^+$ cell line than for $CD4^+$ enriched PBMC, but the peptides eliciting a positive response were in general the same. Fourteen of the 20 peptides most strongly recognized by $CD4^+$ enriched PBMC of subject #4, were among the 20 peptides most strongly recognized by the $CD4^+$ line from the same subject (see boxed peptide designations in FIG. 3). Four of the remaining six peptides recognized by the $CD4^+$ enriched PBMC were also recognized by the $CD4^+$ line, although to a lesser extent than the peptides described above. Two peptides, corresponding to amino acid residues 421–440 (SEQ ID NO:47) and 461–480 (SEQ ID NO:50), recognized by the $CD4^+$ enriched PBMC of subject #4 were not recognized by the $CD4^+$ line in this experiment, possibly due to replicate scattering, but they were recognized in a second experiment, carried out two weeks later. Similar experiments carried out with subject #5 yielded comparable results.

Therefore, the spectrum of peptides recognized by the $CD4^+$ enriched PBMC and $CD4^+$ lines from the same subjects were qualitatively very similar, but the signal to noise ratio was much better for the $CD4^+$ lines. Therefore, $CD4^+$ lines were used for the following studies.

Sequence segments of DTX recognized by anti-DTD T cell lines

The DTX epitopes recognized by the $CD4^+$ cell lines were identified in proliferation assays using individual synthetic DTX-specific peptides. To minimize the potential loss of epitope recognition resulting from biased clonal propagation, the lines were tested for reactivity to individual synthetic peptides as soon as a satisfactory enrichment in reactivity to DTD was obtained, i.e., when the response of the lines to DTD in a proliferation assay was comparable to that of PHA, usually after 3–4 weeks of culture. The consistency of the recognition was verified by repeating the test 1–2 weeks later. For all lines, very similar or identical patterns of peptide recognition were observed in both experiments.

The results obtained in one experiment for each line, testing the response to each individual peptide, are shown in FIG. 4. Although the lines from different subjects showed different degrees of responsiveness to DTX sequences, all subjects recognized a large number of DTX-specific peptide sequences. For all subjects, most of the recognized sequences were within residues 271–450 (SEQ ID NO:57), which form the B fragment, while peptides corresponding to fragment A (amino acids 1–193) (SEQ ID NO:8) were, in general, less immunogenic. Relatively immunodominant sequence segments within fragment A were located at the N terminal region of fragment A, i.e. residues 1–30 (SEQ ID NO:59), and, to a lesser extent, residues 81–120 (SEQ ID NO:60).

Six peptides in the B region were recognized by all seven individuals studied; these peptides comprise residues 271–290 (SEQ. ID NO:2), 321–340 (SEQ. ID NO:3), 331–350 (SEQ. ID NO:4), 351–370 (SEQ. ID NO:5), 411–430 (SEQ. ID NO:6) and 431–450 (SEQ. ID NO:7). Peptides with residues 321–340 (SEQ ID NO:3) and 331–350 ( SEQ ID NO:4) might contain a single $CD4^+$ epitope within their overlap region.

HLA class II restriction

The class II restriction of each IRS was studied in six of the seven subjects, by determining if mAbs against the different class II isotypes affected the response of epitope-specific $CD4^+$ lines to the relevant peptides. As a control for mAb toxicity, the effect of the mAb on the proliferative response induced by IL-2 was determined. As a negative control, triplicate cultures were cultured in the presence of a 20-residue synthetic sequence unrelated to the sequence of peptides with an IRS (residues 1–20 of the TTX light chain sequence) (SEQ ID NO:61).

The results obtained in experiments testing the response of the anti-DTD $CD4^+$ cell lines from two subjects, which are representative of those obtained for all subjects, are shown in FIG. 5. As judged by a significant reduction in cell proliferation in the presence of a mAb against a given class II isotype, most IRSs were presented by two, or all three, class II isotypes. A few IRSs, which were different in different subjects, were presented by one isotype only.

Discussion

Thus, a number of DTX sequence regions are recognized by human $CD4^+$ cells in different subjects. Most $CD4^+$ epitopes are clustered in fragment B of DTX. Although each person had a characteristic pattern of peptide recognition (FIG. 4), six DTX peptide sequences, peptides with residues 271–290 (SEQ. ID NO:2), 321–340 (SEQ. ID NO:3), 331–350 (SEQ. ID NO:4), 351–370 (SEQ. ID NO:5), 411–430 (SEQ. ID NO:6), and 431–450 (SEQ. ID NO:7), were recognized by every individual, irrespective of the class II haplotype. Recognition of an IRS accounted for a substantial fraction of the total response of the $CD4^+$ line to DTX sequences (28–57%, see Table 3). In the two subjects where the $CD4^+$ enriched PBMC response to DTX sequences was investigated, all the IRSs were strongly recognized, at levels comparable to the response induced by DTD, in spite of the overall low level of the response of $CD4^+$ enriched PBMC (FIG. 3). The IRS containing peptides were frequently presented by more than one class II isotype (FIG. 5).

TABLE 3

| Subject # | % of the total response due to the IRS[a] |
| --- | --- |
| 1 | 57 |
| 2 | 51 |
| 3 | 42 |
| 4 | 37 |
| 5 | 43 |
| 6 | 31 |
| 7 | 28 |

[a]The fraction of the total response to DTX peptide sequences due to the response to IRS was determined as follows. Each anti-DTD line was challenged with each individual peptide in triplicate cultures. The basal level of cell proliferation, in the absence of any stimulus, was determined in triplicate cultures containing T line cells and APC only (blanks). The average cpm values obtained for the blanks were subtracted from those obtained for the peptides. The values thus obtained were added up, to yield what was considered 100% stimulation by DTX-specific peptides. The average cpm obtained for each IRS minus blank were added, and the fraction of the total response which this sum represented was calculated.

Preferential recognition of certain epitopes might be due to a biased V (variable) region repertoire of the TCR expressed by that subject, or by all subjects expressing a given class II haplotype. However, this explanation does not hold for the findings reported here, because the IRSs were recognized by subjects of different MHC class II haplotype. The molecular basis of the preferred recognition of the IRS by human CD4[+] cells could be due to the characteristics of the interaction of peptide epitopes with HLA class II molecule, and/or the structural properties of the Ag molecule, which may influence processing and presentation of certain sequence regions.

Many peptide sequences can bind different DR alleles. Nonetheless, the ability of a given Ag sequence to bind most or all DR molecules does not suffice for a peptide to be an IRS (for example, see Manfredi et al., *J. Immunol.*, 152, 4165 (1994); Reece et al., *J. Immunol.*, 151, 6175 (1993)). Factor(s) that are important for an Ag sequence region to be an IRS for CD4[+] cell sensitization include a structural property which gives the IRS an advantage during Ag processing, causing its preferential release from the Ag molecule, and/or availability for class II binding and presentation.

DTX has three distinct domains (Choe et al., supra): the C or catalytic domain (residues 1–193) (SEQ ID NO:8), which is formed by fragment A, the T or transmembrane domain (residues 205–378) (SEQ ID NO:62), and the R or receptor binding domain (residues 386–535) (SEQ ID NO:63). The T and the R domains form fragment B. All IRSs described above are within fragment B: residues 411–430 (SEQ ID NO:6) and 431–450 (SEQ ID NO:7) are part of the R domain, the others are part of the T domain. The T domain includes nine α helices (TH1–TH9), arranged in three antiparallel layers. Helices TH8 and TH9 are unusually apolar and constitute the central core layer. The R domain consists of nine β strands (RB1–RB9). These secondary structure elements are connected by loops. All IRSs include one or more of the α helixes or β sheets described above.

A common structural property of the IRSs that may give them an advantage during DTX processing, is that they all include, or are flanked by, both at the amino and carboxyl terminal ends, sequence regions forming relatively unstructured loops fully exposed to the solvent. These loops may be easily accessible targets for the proteolytic enzymes involved in Ag processing, even in the absence of any substantial denaturation of the Ag.

For example, IRS peptide 271–290 (SEQ ID NO:2) includes the α helix TH5 (residues 275–288) (SEQ ID NO:64), one face of which is exposed to the solvent. TH5 is flanked on its amino terminal end by an exposed loop formed by residues 271–274 (SEQ ID NO:65), and at its carboxyl terminal end by another exposed loop, formed by residues 289–296 (SEQ ID NO:66).

The overlapping IRS peptides 321–340 (SEQ. ID NO:3) and 331–350 (SEQ ID NO:4) (sequence 321–350) (SEQ ID NO:67) include the helix TH8 (residues 326–347) (SEQ ID NO:68), which, although contained in the core of the native DTX molecule, is flanked at both its amino and carboxyl terminal ends by solvent-exposed loops, formed by residues 322–327 (SEQ ID NO:69) and 348–357 (SEQ ID NO:70) respectively. These two overlapping IRS peptides might include only one epitope, within the sequence region forming TH8, which includes the overlap between peptides 321–340 (SEQ ID NO:3) and 331–350 (SEQ ID NO:4) (residues 331–340) (SEQ ID NO:71). In the native DTX molecule, this epitope is flanked by fully exposed loops at either end.

IRS peptide 351–370 (SEQ ID NO:5) includes the majority of the α helix TH9 (residues 358–376) (SEQ ID NO:72), which, although mostly buried in the core of the DTX molecule (it has only one exposed residue), is flanked at both ends by fully exposed loops, namely, the coil regions formed by residue 348–357 (SEQ ID NO:70), between helices TH8 and TH9, and 377–388 (SEQ ID NO:73).

IRS peptide 411–430 (SEQ ID NO:6) includes the β strand RB3 (residues 413–422) (SEQ ID NO:74), several residues of which (423–426) (SEQ ID NO:75), are fully exposed to the solvent. RB3 is preceded, on its amino terminal side, by an exposed loop formed by residues 408–412 (SEQ ID NO:76). Also, at the carboxyl terminal end of IRS 411–430 (SEQ ID NO:6), residues 423–431 (SEQ ID NO:77) form an exposed loop connecting RB3 to RB4.

IRS peptide 431–450 (SEQ ID NO:7) includes the β strand RB4 (431–443) (SEQ ID NO:78). RB4 is followed by an exposed loop (residues 444–448) (SEQ ID NO:79) and is preceded in the DTX molecule by a small exposed loop between RB3 and RB4 (423–431) (SEQ ID NO:77).

Therefore, the present results show that sequence segments "hidden" in the hydrophobic core of a protein Ag might also be important targets of immune recognition by CD4[+] cells, because helices TH8 and TH9, which correspond to IRS 321–340 (SEQ ID NO:83), 331–350 (SEQ ID NO:4), and 351–370 (SEQ ID NO:5), are deep in the core of the DTX molecule. This underscores the importance of flanking exposed loops for IRS formation. These exposed loops would make an easy target for processing enzymes, resulting in the fast release of sequence segments embedded in the hydrophobic core of the Ag molecule.

Because the IRSs are recognized in association with different class II alleles and isotypes, their sequence must have characteristics compatible with binding to a large number of different class II molecules. X-ray diffraction studies of the DR1 molecule indicated that several residues involved in formation of the peptide binding site are conserved in most or all class II isotypes, suggesting that all class II molecules bind peptides with similar mechanisms (Stern et al., *Nature*, 368, 215 (1994); Brown et al., *Nature*, 364, 33 (1993)). In agreement with that prediction, the DTX IRSs were frequently recognized in association with different class II isotypes.

Previous studies, based on sequence alignments of naturally processed peptides, eluted from purified DR molecules, or on the effect on binding to DR of substitutions of individual residues within a peptide sequence, suggested sequence motifs that could be characteristic of binding to a given DR allele, or of "universal" DR binding. Crystallographic studies of the DR1 molecule complexed to a peptide, and binding studies utilizing phage display libraries, thus directly studying any possible sequence of a given length, have identified the structural and sequence properties necessary for a peptide to bind to different DR types (Stern et al., supra; Hammer et al., *Cell*, 74, 197 (1993); Wicherpfenning et al., *J. Exp. Med.*, 181, 1597 (1995); Geluk et al., *Eur. J. Immunol.*, 22, 107 (1995); Hammer et al., *J. Exp. Med.*, 181, 1847 (1995).

Peptides bind to DR molecules in an extended conformation, which allows extensive hydrophobic interactions between the peptide backbone and the binding groove of the DR molecules, thus providing a mode of peptide binding independent of the peptide sequence (Stern et al., supra; Jardetzky et al., *EMBO*, 9, 1797 (1990)). Peptide specificity is due to interactions between pockets on the DR molecules, whose surface have shape and charges characteristic for a given DR allele, and to anchor residues of suitable size, hydropathic properties and charge (Stern et al., supra; Hammer et al., supra).

Although as many as seven anchor residues have been identified, at least for a DR4 subtype, only one or very few residues are crucial for binding (Hammer et al., *PNAS USA*, 91, 4456 (1994)), and the others, while improving the affinity of the binding, tolerate a broad range of substitutions, without obliterating the peptide/DR interaction (Hammer et al., *J. Exp. Med.*, supra; Hammer et al., *PNAS USA*, supra). While anchor residues are frequently uncharged or hydrophobic, both positively and negatively charged anchor residues have been identified for peptide binding to individual DR alleles, fitting in pockets, on the DR molecule, lined by residues of complementary charge. When the lining of DR binding pockets may have charges, the presence of the wrong charge on a peptide residue aligned with that pocket may de-stabilize peptide-DR binding.

While it is unknown which residues within the IRS interact with the different class II molecules, and structural correlates between the sequence of an IRS peptide and its ability to bind to different presenting molecules are not identified, the binding motifs identified for peptide binding to DR1 (Hammer et al., *J. Exp. Med.*, supra), and different DR4 subtypes (Hammer et al., *Cell*, supra; Hammer et al., *J. Exp. Med.*, supra; Jardetzky et al., supra; Sette et al., *J. Immunol.*, 151, 3163 (1993)) present in most or all the DTX IRSs are shown in Table 4.

All the IRSs identified here overlap four of the five DTX sequence segments which are most hydrophobic: four of those segments do not contain any charged residue, and one (segment 353–371) (SEQ ID NO:58) contains a single charge (London et al., *Biochem. Biophys. Acta.*, 1113, 25 (1992)). The relationship between the IRSs and those uncharged DTX sequence regions is illustrated in FIG. 1. However, the uncharged nature of a DTX peptide sequence is not predictive of an IRS, because some peptides which largely overlapped an uncharged sequence region were not recognized by all the subjects. Also, all the IRSs included residues outside the hydrophobic regions described above, some of which are charged.

However, it is possible that the presence of a stretch of uncharged residues might be related with IRS formation, because, uncharged sequence segments might be preferred as "universal" DR binders because unlike charged residues which carry a "wrong" charge that would strongly, negatively affect peptide binding to some class II molecules, the uncharged residues would not have any negative affect on binding.

The complete disclosure of all patents, patent documents and publications cited herein are incorporated herein by reference as if individually incorporated. The foregoing detailed description and examples have been given for clarity or understanding only. No unnecessary limitations are to be understood. The invention is not limited to the exact details shown and described for variation obvious to one skilled in the art will be included within the invention defined by the claims.

What is claimed is:

1. An isolated and purified peptide comprising the amino acid sequence Pro-Val-Phe-Ala-Gly-Ala-Asn-Tyr-Ala-Ala-Trp-Ala-Val-Asn-Val-Ala-Gln-Val-Ile-Asp (SEQ ID NO:2), or an immunogenic fragment or subunit thereof, wherein the peptide consists of no more than 40 amino acid residues.

2. An isolated and purified peptide comprising the amino acid sequence Val-His-His-Asn-Thr-Glu-Glu-Ile-Val-Ala-Gln-Ser-Ile-Ala-Leu-Ser-Ser-Leu-Met-Val (SEQ ID NO:3), or an immunogenic fragment or subunit thereof, wherein the peptide consists of no more than about 40 amino acid residues.

3. An isolated and purified peptide comprising the amino acid sequence Gln-Ser-Ile-Ala-Leu-Ser-Ser-Leu-Met-Val-Ala-Gln-Ala-Ile-Pro-Leu-Val-Gly-Glu-Leu (SEQ ID NO:4), or an immunogenic fragment or subunit thereof, wherein the peptide consists of no more than about 40 amino acid residues.

4. An isolated and purified peptide comprising the amino acid sequence Val-Asp-Ile-Gly-Phe-Ala-Ala-Tyr-Asn-Phe-Val-Glu-Ser-Ile-Ile-Asn-Leu-Phe-Gln-Val-Val (SEQ ID NO:5), or an immunogenic fragment or subunit thereof, wherein the peptide consists of no more than about 40 amino acid residues.

5. An isolated and purified peptide comprising the amino acid sequence Gln-Gly-Glu-Ser-Gly-His-Asp-Ile-Lys-Ile-Thr-Ala-Glu-Asn-Thr-Pro-Leu-Pro-Ile-Ala (SEQ ID NO:6), or an immunogenic fragment or subunit thereof, wherein the peptide consists of no more than about 40 amino acid residues.

6. An isolated and purified peptide comprising the amino acid sequence Gly-Val-Leu-Leu-Pro-Thr-Ile-Pro-Gly-Lys-Leu-Asp-Val-Asn-Lys-Ser-Lys-Thr-His-Ile (SEQ ID NO:7), or an immunogenic fragment or subunit thereof, wherein the peptide consists of no more than about 40 amino acid residues.

7. An isolated and purified peptide comprising an amino acid sequence homologous or identical to a portion of the amino acid sequence of diphtheria toxin, wherein the peptide has at least 7 and at most 40 amino acid residues, wherein a portion of the amino acid sequence in the peptide contains a contiguous sequence of amino acid residues that form at least a portion of one alpha helix or a beta sheet in vitro or in vivo, which peptide comprises an immunodominant region sequence.

8. The isolated peptide of claim 7 which comprises a sequence region that is present on the surface of crystallized diphtheria toxin.

9. A vaccine comprising an immunogenic amount of at least one diphtheria toxin-specific peptide containing an immunodominant region sequence, wherein the peptide is combined with a physiologically acceptable, non-toxic liquid vehicle, which amount is effective to immunize a susceptible mammal against *Corynebacterium diphtheriae*, wherein the peptide has at least 7 and at most 40 amino acid residues.

10. The vaccine of claim 9 wherein the mammal is a human.

11. The vaccine of claim 9 which further comprises an amount of diptheria toxoid effective to increase the immunogenic response to the vaccine.

12. An immunogenic composition comprising a peptide linked to a non- or poorly immunogenic molecule, wherein the peptide comprises an amino acid sequence homologous or identical to a portion of the amino acid sequence of diphtheria toxin, wherein the peptide comprises an immunodominant region sequence, and wherein the peptide has at least 7 and at most 40 amino acid residues.

13. An immunogenic composition comprising a peptide linked to a non- or poorly immunogenic molecule, wherein the peptide comprises a contiguous amino acid sequence that is present on the surface of crystallized diphtheria toxin, wherein the peptide consists of no more than about 40 amino acid residues, and wherein the peptide comprises an immunodominant region sequence.

14. The isolated and purified peptide of claim 7 wherein the amino acid sequence of diphtheria toxin comprises SEQ ID NO:1.

15. The immunogenic composition of claim 12 wherein the amino acid of diphtheria toxin comprises SEQ ID NO:1.

* * * * *

SEQUENCE LISTING ( 1 ) GENERAL INFORMATION:

( i i i ) NUMBER OF SEQUENCES: 79

( 2 ) INFORMATION FOR SEQ ID NO:1:

( i ) SEQUENCE CHARACTERISTICS:
        ( A ) LENGTH: 535 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:1:

```
Gly  Ala  Asp  Asp  Val  Val  Asp  Ser  Ser  Lys  Ser  Phe  Val  Met  Glu  Asn
 1                   5                        10                       15
```

```
Phe  Ser  Ser  Tyr  His  Gly  Thr  Lys  Pro  Gly  Tyr  Val  Asp  Ser  Ile  Gln
               20                  25                       30

Lys  Gly  Ile  Gln  Lys  Pro  Lys  Ser  Gly  Thr  Gln  Gly  Asn  Tyr  Asp  Asp
          35                  40                       45

Asp  Trp  Lys  Gly  Phe  Tyr  Ser  Thr  Asp  Asn  Lys  Tyr  Asp  Ala  Ala  Gly
     50                  55                  60

Tyr  Ser  Val  Asp  Asn  Glu  Asn  Pro  Leu  Ser  Gly  Lys  Ala  Gly  Gly  Val
65                  70                       75                            80

Val  Lys  Val  Thr  Tyr  Pro  Gly  Leu  Thr  Lys  Val  Leu  Ala  Leu  Lys  Val
               85                       90                            95

Asp  Asn  Ala  Glu  Thr  Ile  Lys  Lys  Glu  Leu  Gly  Leu  Ser  Leu  Thr  Glu
               100                 105                      110

Pro  Leu  Met  Glu  Gln  Val  Gly  Thr  Glu  Glu  Phe  Ile  Lys  Arg  Phe  Gly
          115                 120                      125

Asp  Gly  Ala  Ser  Arg  Val  Val  Leu  Ser  Leu  Pro  Phe  Ala  Glu  Gly  Ser
          130                 135                      140

Ser  Ser  Val  Glu  Tyr  Ile  Asn  Asn  Trp  Glu  Gln  Ala  Lys  Ala  Leu  Ser
145                      150                      155                      160

Val  Glu  Leu  Glu  Ile  Asn  Phe  Glu  Thr  Arg  Gly  Lys  Arg  Gly  Gln  Asp
               165                      170                      175

Ala  Met  Tyr  Glu  Tyr  Met  Ala  Gln  Ala  Cys  Ala  Gly  Asn  Arg  Val  Arg
               180                 185                      190

Arg  Ser  Val  Gly  Ser  Ser  Leu  Ser  Cys  Ile  Asn  Leu  Asp  Trp  Asp  Val
               195                 200                      205

Ile  Arg  Asp  Lys  Thr  Lys  Thr  Lys  Ile  Glu  Ser  Leu  Lys  Glu  His  Gly
     210                 215                      220

Pro  Ile  Lys  Asn  Lys  Met  Ser  Glu  Ser  Pro  Asn  Lys  Thr  Val  Ser  Glu
225                      230                 235                           240

Glu  Lys  Ala  Lys  Gln  Tyr  Leu  Glu  Glu  Phe  His  Gln  Thr  Ala  Leu  Glu
               245                      250                      255

His  Pro  Glu  Leu  Ser  Glu  Leu  Lys  Thr  Val  Thr  Gly  Thr  Asn  Pro  Val
               260                      265                      270

Phe  Ala  Gly  Ala  Asn  Tyr  Ala  Ala  Trp  Ala  Val  Asn  Val  Ala  Gln  Val
          275                      280                 285

Ile  Asp  Ser  Glu  Thr  Ala  Asp  Asn  Leu  Glu  Lys  Thr  Thr  Ala  Ala  Leu
     290                      295                      300

Ser  Ile  Leu  Pro  Gly  Ile  Gly  Ser  Val  Met  Gly  Ile  Ala  Asp  Gly  Ala
305                 310                      315                           320

Val  His  His  Asn  Thr  Glu  Glu  Ile  Val  Ala  Gln  Ser  Ile  Ala  Leu  Ser
                    325                      330                      335

Ser  Leu  Met  Val  Ala  Gln  Ala  Ile  Pro  Leu  Val  Gly  Glu  Leu  Val  Asp
               340                 345                      350

Ile  Gly  Phe  Ala  Ala  Tyr  Asn  Phe  Val  Glu  Ser  Ile  Ile  Asn  Leu  Phe
          355                      360                 365

Gln  Val  Val  His  Asn  Ser  Tyr  Asn  Arg  Pro  Ala  Tyr  Ser  Pro  Gly  His
          370                 375                      380

Lys  Thr  Gln  Pro  Phe  Leu  His  Asp  Gly  Tyr  Ala  Val  Ser  Trp  Asn  Thr
385                      390                 395                           400

Val  Glu  Asp  Ser  Ile  Ile  Arg  Thr  Gly  Phe  Gln  Gly  Glu  Ser  Gly  His
                    405                      410                      415

Asp  Ile  Lys  Ile  Thr  Ala  Glu  Asn  Thr  Pro  Leu  Pro  Ile  Ala  Gly  Val
               420                      425                      430
```

| Leu | Leu | Pro<br>435 | Thr | Ile | Pro | Gly | Lys<br>440 | Leu | Asp | Val | Asn<br>445 | Lys | Ser | Lys | Thr |
|---|---|---|---|---|---|---|---|---|---|---|---|---|---|---|---|
| His | Ile<br>450 | Ser | Val | Asn | Gly | Arg<br>455 | Lys | Ile | Arg | Met | Arg<br>460 | Cys | Arg | Ala | Ile |
| Asp<br>465 | Gly | Asp | Val | Thr | Phe<br>470 | Cys | Arg | Pro | Lys | Ser<br>475 | Pro | Val | Tyr | Val | Gly<br>480 |
| Asn | Gly | Val | His | Ala<br>485 | Asn | Leu | His | Val | Ala<br>490 | Phe | His | Arg | Ser | Ser<br>495 | Ser |
| Glu | Lys | Ile | His<br>500 | Ser | Asn | Glu | Ile | Ser<br>505 | Ser | Asp | Ser | Ile | Gly<br>510 | Val | Leu |
| Gly | Tyr | Gln<br>515 | Lys | Thr | Val | Asp | His<br>520 | Thr | Lys | Val | Asn | Ser<br>525 | Lys | Leu | Ser |
| Leu | Phe<br>530 | Phe | Glu | Ile | Lys | Ser<br>535 | | | | | | | | | |

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

| Pro<br>1 | Val | Phe | Ala | Gly<br>5 | Ala | Asn | Tyr | Ala | Ala<br>10 | Trp | Ala | Val | Asn | Val<br>15 | Ala |
|---|---|---|---|---|---|---|---|---|---|---|---|---|---|---|---|
| Gln | Val | Ile | Asp<br>20 | | | | | | | | | | | | |

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:3:

| Val<br>1 | His | His | Asn | Thr<br>5 | Glu | Glu | Ile | Val | Ala<br>10 | Gln | Ser | Ile | Ala | Leu<br>15 | Ser |
|---|---|---|---|---|---|---|---|---|---|---|---|---|---|---|---|
| Ser | Leu | Met | Val<br>20 | | | | | | | | | | | | |

( 2 ) INFORMATION FOR SEQ ID NO:4:

( i ) SEQUENCE CHARACTERISTICS:
        ( A ) LENGTH: 20 amino acids (B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:4:

| Gln | Ser | Ile | Ala | Leu | Ser | Ser | Leu | Met | Val | Ala | Gln | Ala | Ile | Pro | Leu |
|---|---|---|---|---|---|---|---|---|---|---|---|---|---|---|---|
| 1 | | | | 5 | | | | | 10 | | | | | 15 | |

| Val | Gly | Glu | Leu |
|---|---|---|---|
| | | | 20 |

(2) INFORMATION FOR SEQ ID NO:5:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:5:

| Val | Asp | Ile | Gly | Phe | Ala | Ala | Tyr | Asn | Phe | Val | Glu | Ser | Ile | Ile | Asn |
|---|---|---|---|---|---|---|---|---|---|---|---|---|---|---|---|
| 1 | | | | 5 | | | | | 10 | | | | | 15 | |

| Leu | Phe | Gln | Val |
|---|---|---|---|
| | | | 20 |

(2) INFORMATION FOR SEQ ID NO:6:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

| Gln | Gly | Glu | Ser | Gly | His | Asp | Ile | Lys | Ile | Thr | Ala | Glu | Asn | Thr | Pro |
|---|---|---|---|---|---|---|---|---|---|---|---|---|---|---|---|
| 1 | | | | 5 | | | | | 10 | | | | | 15 | |

| Leu | Pro | Ile | Ala |
|---|---|---|---|
| | | | 20 |

(2) INFORMATION FOR SEQ ID NO:7:

(i) SEQUENCE CHARACTERISTICS:

(A) LENGTH: 20 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:7:

| Gly | Val | Leu | Leu | Pro | Thr | Ile | Pro | Gly | Lys | Leu | Asp | Val | Asn | Lys | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Lys | Thr | His | Ile |
|-----|-----|-----|-----|
|     |     |     | 20  |

(2) INFORMATION FOR SEQ ID NO:8:

(i) SEQUENCE CHARACTERISTICS:
(A) LENGTH: 193 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:8:

| Gly | Ala | Asp | Asp | Val | Val | Asp | Ser | Ser | Lys | Ser | Phe | Val | Met | Glu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Ser | Ser | Tyr | His | Gly | Thr | Lys | Pro | Gly | Tyr | Val | Asp | Ser | Ile | Gln |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Lys | Gly | Ile | Gln | Lys | Pro | Lys | Ser | Gly | Thr | Gln | Gly | Asn | Tyr | Asp | Asp |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Asp | Trp | Lys | Gly | Phe | Tyr | Ser | Thr | Asp | Asn | Lys | Tyr | Asp | Ala | Ala | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Tyr | Ser | Val | Asp | Asn | Glu | Asn | Pro | Leu | Ser | Gly | Lys | Ala | Gly | Gly | Val |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Val | Lys | Val | Thr | Tyr | Pro | Gly | Leu | Thr | Lys | Val | Leu | Ala | Leu | Lys | Val |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asp | Asn | Ala | Glu | Thr | Ile | Lys | Lys | Glu | Leu | Gly | Leu | Ser | Leu | Thr | Glu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Pro | Leu | Met | Glu | Gln | Val | Gly | Thr | Glu | Glu | Phe | Ile | Lys | Arg | Phe | Gly |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Asp | Gly | Ala | Ser | Arg | Val | Val | Leu | Ser | Leu | Pro | Phe | Ala | Glu | Gly | Ser |
|-----|-----|-----|-----|-----|-----|-----|-----|-----|-----|-----|-----|-----|-----|-----|-----|
|     |     | 130 |     |     |     | 135 |     |     |     |     | 140 |     |     |     |     |

| Ser | Ser | Val | Glu | Tyr | Ile | Asn | Asn | Trp | Glu | Gln | Ala | Lys | Ala | Leu | Ser |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Val | Glu | Leu | Glu | Ile | Asn | Phe | Glu | Thr | Arg | Gly | Lys | Arg | Gly | Gln | Asp |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ala | Met | Tyr | Glu | Tyr | Met | Ala | Gln | Ala | Cys | Ala | Gly | Asn | Arg | Val | Arg |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

Arg (2) INFORMATION FOR SEQ ID NO:9:

(i) SEQUENCE CHARACTERISTICS:
        (A) LENGTH: 331 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:9:

```
Asp Trp Asp Val Ile Arg Asp Lys Thr Lys Thr Lys Ile Glu Ser Leu
 1               5                  10                  15
Lys Glu His Gly Pro Ile Lys Asn Lys Met Ser Glu Ser Pro Asn Lys
            20                  25                  30
Thr Val Ser Glu Glu Lys Ala Lys Gln Tyr Leu Glu Glu Phe His Gln
            35                  40                  45
Thr Ala Leu Glu His Pro Glu Leu Ser Glu Leu Lys Thr Val Thr Gly
 50                  55                  60
Thr Asn Pro Val Phe Ala Gly Ala Asn Tyr Ala Ala Trp Ala Val Asn
 65                  70                  75                  80
Val Ala Gln Val Ile Asp Ser Glu Thr Ala Asp Asn Leu Glu Lys Thr
                    85                  90                  95
Thr Ala Ala Leu Ser Ile Leu Pro Gly Ile Gly Ser Val Met Gly Ile
                100                 105                 110
Ala Asp Gly Ala Val His His Asn Thr Glu Glu Ile Val Ala Gln Ser
            115                 120                 125
Ile Ala Leu Ser Ser Leu Met Val Ala Gln Ala Ile Pro Leu Val Gly
 130                 135                 140
Glu Leu Val Asp Ile Gly Phe Ala Ala Tyr Asn Phe Val Glu Ser Ile
 145                 150                 155                 160
Ile Asn Leu Phe Gln Val Val His Asn Ser Tyr Asn Arg Pro Ala Tyr
                165                 170                 175
Ser Pro Gly His Lys Thr Gln Pro Phe Leu His Asp Gly Tyr Ala Val
                180                 185                 190
Ser Trp Asn Thr Val Glu Asp Ser Ile Ile Arg Thr Gly Phe Gln Gly
            195                 200                 205
Glu Ser Gly His Asp Ile Lys Ile Thr Ala Glu Asn Thr Pro Leu Pro
 210                 215                 220
Ile Ala Gly Val Leu Leu Pro Thr Ile Pro Gly Lys Leu Asp Val Asn
 225                 230                 235                 240
Lys Ser Lys Thr His Ile Ser Val Asn Gly Arg Lys Ile Arg Met Arg
                245                 250                 255
Cys Arg Ala Ile Asp Gly Asp Val Thr Phe Cys Arg Pro Lys Ser Pro
                260                 265                 270
Val Tyr Val Gly Asn Gly Val His Ala Asn Leu His Val Ala Phe His
            275                 280                 285
Arg Ser Ser Ser Glu Lys Ile His Ser Asn Glu Ile Ser Ser Asp Ser
 290                 295                 300
```

| Ile | Gly | Val | Leu | Gly | Tyr | Gln | Lys | Thr | Val | Asp | His | Thr | Lys | Val | Asn |
| 305 | | | | 310 | | | | | 315 | | | | | | 320 |

| Ser | Lys | Leu | Ser | Leu | Phe | Phe | Glu | Ile | Lys | Ser |
| | | | | 325 | | | | | 330 | |

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:10:

| Gly | Ala | Asp | Asp | Val | Val | Asp | Ser | Ser | Lys | Ser | Phe | Val | Met | Glu | Asn |
| 1 | | | | 5 | | | | | 10 | | | | | 15 | |

| Phe | Ser | Ser | Tyr |
| | | | 20 |

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:11:

| Ser | Phe | Val | Met | Glu | Asn | Phe | Ser | Ser | Tyr | His | Gly | Thr | Lys | Pro | Gly |
| 1 | | | | 5 | | | | | 10 | | | | | 15 | |

| Tyr | Val | Asp | Ser |
| | | | 20 |

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:12:

His Gly Thr Lys Pro Gly Tyr Val Asp Ser Ile Gln Lys Gly Ile Gln
1               5                   10                  15

Lys Pro Lys Ser
            20

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:13:

Ile Gln Lys Gly Ile Gln Lys Pro Lys Ser Gly Thr Gln Gly Asn Tyr
1               5                   10                  15

Asp Asp Asp Trp
            20

(2) INFORMATION FOR SEQ ID NO:14:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:14:

Gly Thr Gln Gly Asn Tyr Asp Asp Asp Trp Lys Gly Phe Tyr Ser Thr
1               5                   10                  15

Asp Asn Lys Tyr
            20

(2) INFORMATION FOR SEQ ID NO:15:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

( x i ) SEQUENCE DESCRIPTION: SEQ ID NO:15:

Lys Gly Phe Tyr Ser Thr Asp Asn Lys Tyr Asp Ala Ala Gly Tyr Ser
1               5                   10                  15

Val Asp Asn Glu
            20

( 2 ) INFORMATION FOR SEQ ID NO:16:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:16:

Asp Ala Ala Gly Tyr Ser Val Asp Asn Glu Asn Pro Leu Ser Gly Lys
1               5                   10                  15

Ala Gly Gly Val
            20

( 2 ) INFORMATION FOR SEQ ID NO:17:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:17:

Asn Pro Leu Ser Gly Lys Ala Gly Gly Val Val Lys Val Thr Tyr Pro
1               5                   10                  15

Gly Leu Thr Lys
            20

( 2 ) INFORMATION FOR SEQ ID NO:18:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:18:

Val Lys Val Thr Tyr Pro Gly Leu Thr Lys Val Leu Ala Leu Lys Val
1               5                   10                  15

Asp Asn Ala Glu
            20

( 2 ) INFORMATION FOR SEQ ID NO:19:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:19:

Val Leu Ala Leu Lys Val Asp Asn Ala Glu Thr Ile Lys Lys Glu Leu
1               5                   10                  15

Gly Leu Ser Leu
            20

( 2 ) INFORMATION FOR SEQ ID NO:20:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:20:

Thr Ile Lys Lys Glu Leu Gly Leu Ser Leu Thr Glu Pro Leu Met Glu
1               5                   10                  15

Gln Val Gly Thr
            20

( 2 ) INFORMATION FOR SEQ ID NO:21:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:21:

Thr Glu Pro Leu Met Glu Gln Val Gly Thr Glu Glu Phe Ile Lys Arg
1               5                   10                  15
Phe Gly Asp Gly
            20

( 2 ) INFORMATION FOR SEQ ID NO:22:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:22:

Glu Glu Phe Ile Lys Arg Phe Gly Asp Gly Ala Ser Arg Val Val Leu
1               5                   10                  15
Ser Leu Pro Phe
            20

( 2 ) INFORMATION FOR SEQ ID NO:23:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:23:

Ala Ser Arg Val Val Leu Ser Leu Pro Phe Ala Glu Gly Ser Ser Ser
1               5                   10                  15
Val Glu Tyr Ile
            20

( 2 ) INFORMATION FOR SEQ ID NO:24:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal (vi) ORIGINAL SOURCE:

(xi) SEQUENCE DESCRIPTION: SEQ ID NO:24:

| Ala | Glu | Gly | Ser | Ser | Ser | Val | Glu | Tyr | Ile | Asn | Asn | Trp | Glu | Gln | Ala |
|---|---|---|---|---|---|---|---|---|---|---|---|---|---|---|---|
| 1 | | | | 5 | | | | | 10 | | | | | 15 | |

| Lys | Ala | Leu | Ser |
|---|---|---|---|
| | | | 20 |

(2) INFORMATION FOR SEQ ID NO:25:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:25:

| Asn | Asn | Trp | Glu | Gln | Ala | Lys | Ala | Leu | Ser | Val | Glu | Leu | Glu | Ile | Asn |
|---|---|---|---|---|---|---|---|---|---|---|---|---|---|---|---|
| 1 | | | | 5 | | | | | 10 | | | | | 15 | |

| Phe | Glu | Thr | Arg |
|---|---|---|---|
| | | | 20 |

(2) INFORMATION FOR SEQ ID NO:26:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:26:

| Val | Glu | Leu | Glu | Ile | Asn | Phe | Glu | Thr | Arg | Gly | Lys | Arg | Gly | Gln | Asp |
|---|---|---|---|---|---|---|---|---|---|---|---|---|---|---|---|
| 1 | | | | 5 | | | | | 10 | | | | | 15 | |

| Ala | Met | Tyr | Glu |
|---|---|---|---|
| | | | 20 |

(2) INFORMATION FOR SEQ ID NO:27:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO ( v ) FRAGMENT TYPE: internal ( v i ) ORIGINAL SOURCE:

( x i ) SEQUENCE DESCRIPTION: SEQ ID NO:27:

Gly Lys Arg Gly Gln Asp Ala Met Tyr Glu Tyr Met Ala Gln Ala Cys
1               5                   10                  15

Ala Gly Asn Arg
            20

( 2 ) INFORMATION FOR SEQ ID NO:28:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:28:

Tyr Met Ala Gln Ala Cys Ala Gly Asn Arg Val Arg Arg Ser Val Gly
1               5                   10                  15

Ser Ser Leu Ser
            20

( 2 ) INFORMATION FOR SEQ ID NO:29:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:29:

Val Arg Arg Ser Val Gly Ser Ser Leu Ser Cys Ile Asn Leu Asp Trp
1               5                   10                  15

Asp Val Ile Arg
            20

( 2 ) INFORMATION FOR SEQ ID NO:30:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:30:

Cys Ile Asn Leu Asp Trp Asp Val Ile Arg Asp Lys Thr Lys Thr Lys
1               5                   10                  15
Ile Glu Ser Leu
            20

( 2 ) INFORMATION FOR SEQ ID NO:31:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:31:

Asp Lys Thr Lys Thr Lys Ile Glu Ser Leu Lys Glu His Gly Pro Ile
1               5                   10                  15
Lys Asn Lys Met
            20

( 2 ) INFORMATION FOR SEQ ID NO:32:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:32:

Lys Glu His Gly Pro Ile Lys Asn Lys Met Ser Glu Ser Pro Asn Lys
1               5                   10                  15
Thr Val Ser Glu
            20

( 2 ) INFORMATION FOR SEQ ID NO:33:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:33:

Ser Glu Ser Pro Asn Lys Thr Val Ser Glu Glu Lys Ala Lys Gln Tyr
1               5                   10                  15

Leu Glu Glu Phe
            20

(2) INFORMATION FOR SEQ ID NO:34:

(i) SEQUENCE CHARACTERISTICS:
        (A) LENGTH: 20 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:34:

Glu Lys Ala Lys Gln Tyr Leu Glu Glu Phe His Gln Thr Ala Leu Glu
1               5                   10                  15

His Pro Glu Leu
            20

(2) INFORMATION FOR SEQ ID NO:35:

(i) SEQUENCE CHARACTERISTICS:
        (A) LENGTH: 20 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:35:

His Gln Thr Ala Leu Glu His Pro Glu Leu Ser Glu Leu Lys Thr Val
1               5                   10                  15

Thr Gly Thr Asn
            20

(2) INFORMATION FOR SEQ ID NO:36:

(i) SEQUENCE CHARACTERISTICS:
        (A) LENGTH: 20 amino acids
        (B) TYPE: amino acid
        (C) STRANDEDNESS: single
        (D) TOPOLOGY: linear (i i) MOLECULE TYPE: peptide (i i i) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:36:

Ser Glu Leu Lys Thr Val Thr Gly Thr Asn Pro Val Phe Ala Gly Ala
1               5                   10                  15
Asn Tyr Ala Ala
            20

(2) INFORMATION FOR SEQ ID NO:37:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:37:

Trp Ala Val Asn Val Ala Gln Val Ile Asp Ser Glu Thr Ala Asp Asn
1               5                   10                  15
Leu Glu Lys Thr
            20

(2) INFORMATION FOR SEQ ID NO:38:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:38:

Ser Glu Thr Ala Asp Asn Leu Glu Lys Thr Thr Ala Ala Leu Ser Ile
1               5                   10                  15
Leu Pro Gly Ile
            20

(2) INFORMATION FOR SEQ ID NO:39:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:39:

```
Thr Ala Ala Leu Ser Ile Leu Pro Gly Ile Gly Ser Val Met Gly Ile
  1               5                  10                  15
Ala Asp Gly Ala
           20
```

(2) INFORMATION FOR SEQ ID NO:40:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:40:

```
Gly Ser Val Met Gly Ile Ala Asp Gly Ala Val His His Asn Thr Glu
  1               5                  10                  15
Glu Ile Val Ala
           20
```

(2) INFORMATION FOR SEQ ID NO:41:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:41:

```
Ala Gln Ala Ile Pro Leu Val Gly Glu Leu Val Asp Ile Gly Phe Ala
  1               5                  10                  15
Ala Tyr Asn Phe
           20
```

(2) INFORMATION FOR SEQ ID NO:42:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:42:

| Val | Glu | Ser | Ile | Ile | Asn | Leu | Phe | Gln | Val | Val | His | Asn | Ser | Tyr | Asn |
|---|---|---|---|---|---|---|---|---|---|---|---|---|---|---|---|
| 1 | | | | 5 | | | | | 10 | | | | | 15 | |

| Arg | Pro | Ala | Tyr |
|---|---|---|---|
| | | | 20 |

( 2 ) INFORMATION FOR SEQ ID NO:43:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:43:

| Val | His | Asn | Ser | Tyr | Asn | Arg | Pro | Ala | Tyr | Ser | Pro | Gly | His | Lys | Thr |
|---|---|---|---|---|---|---|---|---|---|---|---|---|---|---|---|
| 1 | | | | 5 | | | | | 10 | | | | | 15 | |

| Gln | Pro | Phe | Leu |
|---|---|---|---|
| | | | 20 |

( 2 ) INFORMATION FOR SEQ ID NO:44:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:44:

| Ser | Pro | Gly | His | Lys | Thr | Gln | Pro | Phe | Leu | His | Asp | Gly | Tyr | Ala | Val |
|---|---|---|---|---|---|---|---|---|---|---|---|---|---|---|---|
| 1 | | | | 5 | | | | | 10 | | | | | 15 | |

| Ser | Trp | Asn | Thr |
|---|---|---|---|
| | | | 20 |

( 2 ) INFORMATION FOR SEQ ID NO:45:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:45:

His Asp Gly Tyr Ala Val Ser Trp Asn Thr Val Glu Asp Ser Ile Ile
1               5                   10                  15
Arg Thr Gly Phe
            20

(2) INFORMATION FOR SEQ ID NO:46:

(i) SEQUENCE CHARACTERISTICS:
    (A) LENGTH: 20 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:46:

Val Glu Asp Ser Ile Ile Arg Thr Gly Phe Gln Gly Glu Ser Gly His
1               5                   10                  15
Asp Ile Lys Ile
            20

(2) INFORMATION FOR SEQ ID NO:47:

(i) SEQUENCE CHARACTERISTICS:
    (A) LENGTH: 20 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:47:

Thr Ala Glu Asn Thr Pro Leu Pro Ile Ala Gly Val Leu Leu Pro Thr
1               5                   10                  15
Ile Pro Gly Lys
            20

(2) INFORMATION FOR SEQ ID NO:48:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:48:

```
Leu Asp Val Asn Lys Ser Lys Thr His Ile Ser Val Asn Gly Arg Lys
 1               5                  10                  15
Ile Arg Met Arg
            20
```

(2) INFORMATION FOR SEQ ID NO:49:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:49:

```
Ser Val Asn Gly Arg Lys Ile Arg Met Arg Cys Arg Ala Ile Asp Gly
 1               5                  10                  15
Asp Val Thr Phe
            20
```

(2) INFORMATION FOR SEQ ID NO:50:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:50:

```
Cys Arg Ala Ile Asp Gly Asp Val Thr Phe Cys Arg Pro Lys Ser Pro
 1               5                  10                  15
Val Tyr Val Gly
            20
```

(2) INFORMATION FOR SEQ ID NO:51:

(i) SEQUENCE CHARACTERISTICS:
        (A) LENGTH: 20 amino acids
        (B) TYPE: amino acid
        (C) STRANDEDNESS: single (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:51:

```
Cys Arg Pro Lys Ser Pro Val Tyr Val Gly Asn Gly Val His Ala Asn
 1               5                  10                  15
Leu His Val Ala
            20
```

(2) INFORMATION FOR SEQ ID NO:52:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:52:

```
Asn Gly Val His Ala Asn Leu His Val Ala Phe His Arg Ser Ser Ser
 1               5                  10                  15
Glu Lys Ile His
            20
```

(2) INFORMATION FOR SEQ ID NO:53:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:53:

```
Phe His Arg Ser Ser Ser Glu Lys Ile His Ser Asn Glu Ile Ser Ser
 1               5                  10                  15
Asp Ser Ile Gly
            20
```

(2) INFORMATION FOR SEQ ID NO:54:

(i) SEQUENCE CHARACTERISTICS:
(A) LENGTH: 20 amino acids
(B) TYPE: amino acid ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:54:

Ser  Asn  Glu  Ile  Ser  Ser  Asp  Ser  Ile  Gly  Val  Leu  Gly  Tyr  Gln  Lys
1                   5                        10                       15
Thr  Val  Asp  His
            20

( 2 ) INFORMATION FOR SEQ ID NO:55:

( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:55:

Val  Leu  Gly  Tyr  Gln  Lys  Thr  Val  Asp  His  Thr  Lys  Val  Asn  Ser  Lys
1                   5                        10                       15
Leu  Ser  Leu  Phe
            20

( 2 ) INFORMATION FOR SEQ ID NO:56:

( i ) SEQUENCE CHARACTERISTICS:
            ( A ) LENGTH: 15 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:56:

Thr  Lys  Val  Asn  Ser  Lys  Leu  Ser  Leu  Phe  Phe  Glu  Ile  Lys  Ser
1                   5                        10                       15

( 2 ) INFORMATION FOR SEQ ID NO:57:

( i ) SEQUENCE CHARACTERISTICS:
            ( A ) LENGTH: 180 amino acids
            ( B ) TYPE: amino acid
            ( C ) STRANDEDNESS: single
            ( D ) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:57:

```
Pro Val Phe Ala Gly Ala Asn Tyr Ala Ala Trp Ala Val Asn Val Ala
 1               5                  10                  15
Gln Val Ile Asp Ser Glu Thr Ala Asp Asn Leu Glu Lys Thr Thr Ala
            20                  25                  30
Ala Leu Ser Ile Leu Pro Gly Ile Gly Ser Val Met Gly Ile Ala Asp
        35                  40                  45
Gly Ala Val His His Asn Thr Glu Glu Ile Val Ala Gln Ser Ile Ala
    50                  55                  60
Leu Ser Ser Leu Met Val Ala Gln Ala Ile Pro Leu Val Gly Glu Leu
65                  70                  75                  80
Val Asp Ile Gly Phe Ala Ala Tyr Asn Phe Val Glu Ser Ile Ile Asn
                85                  90                  95
Leu Phe Gln Val Val His Asn Ser Tyr Asn Arg Pro Ala Tyr Ser Pro
            100                 105                 110
Gly His Lys Thr Gln Pro Phe Leu His Asp Gly Tyr Ala Val Ser Trp
        115                 120                 125
Asn Thr Val Glu Asp Ser Ile Ile Arg Thr Gly Phe Gln Gly Glu Ser
    130                 135                 140
Gly His Asp Ile Lys Ile Thr Ala Glu Asn Thr Pro Leu Pro Ile Ala
145                 150                 155                 160
Gly Val Leu Leu Pro Thr Ile Pro Gly Lys Leu Asp Val Asn Lys Ser
                165                 170                 175
Lys Thr His Ile
            180
```

(2) INFORMATION FOR SEQ ID NO:58:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:58:

```
Ile Gly Phe Ala Ala Tyr Asn Phe Val Glu Ser Ile Ile Asn Leu Phe
 1               5                  10                  15
Gln Val Val
```

(2) INFORMATION FOR SEQ ID NO:59:

(i) SEQUENCE CHARACTERISTICS:
(A) LENGTH: 30 amino acids (B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:59:

```
Gly Ala Asp Asp Val Val Asp Ser Ser Lys Ser Phe Val Met Glu Asn
 1               5                  10                  15
Phe Ser Ser Tyr His Gly Thr Lys Pro Gly Tyr Val Asp Ser
            20                  25                  30
```

(2) INFORMATION FOR SEQ ID NO:60:

(i) SEQUENCE CHARACTERISTICS:
(A) LENGTH: 39 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:60:

```
Val Lys Val Thr Tyr Pro Gly Leu Thr Lys Val Leu Ala Leu Lys Val
 1               5                  10                  15
Asp Asn Ala Glu Thr Ile Lys Lys Glu Leu Gly Leu Ser Leu Glu Pro
            20                  25                  30
Leu Met Glu Gln Val Gly Thr
            35
```

(2) INFORMATION FOR SEQ ID NO:61:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:61:

```
Pro Ile Thr Ile Asn Asn Phe Arg Tyr Ser Asp Pro Val Asn Asn Asp
 1               5                  10                  15
Thr Ile Ile Met
            20
```

( 2 ) INFORMATION FOR SEQ ID NO:62:

( i ) SEQUENCE CHARACTERISTICS:
        ( A ) LENGTH: 174 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:62:

```
Asp Trp Asp Val Ile Arg Asp Lys Thr Lys Thr Lys Ile Glu Ser Leu
 1               5                  10                  15
Lys Glu His Gly Pro Ile Lys Asn Lys Met Ser Glu Ser Pro Asn Lys
             20                  25                  30
Thr Val Ser Glu Glu Lys Ala Lys Gln Tyr Leu Glu Glu Phe His Gln
             35                  40                  45
Thr Ala Leu Glu His Pro Glu Leu Ser Glu Leu Lys Thr Val Thr Gly
         50                  55                  60
Thr Asn Pro Val Phe Ala Gly Ala Asn Tyr Ala Ala Trp Ala Val Asn
 65                  70                  75                  80
Val Ala Gln Val Ile Asp Ser Glu Thr Ala Asp Asn Leu Glu Lys Thr
                 85                  90                  95
Thr Ala Ala Leu Ser Ile Leu Pro Gly Ile Gly Ser Val Met Gly Ile
             100                 105                 110
Ala Asp Gly Ala Val His His Asn Thr Glu Glu Ile Val Ala Gln Ser
             115                 120                 125
Ile Ala Leu Ser Ser Leu Met Val Ala Gln Ala Ile Pro Leu Val Gly
     130                 135                 140
Glu Leu Val Asp Ile Gly Phe Ala Ala Tyr Asn Phe Val Glu Ser Ile
145                 150                 155                 160
Ile Asn Leu Phe Gln Val Val His Asn Ser Tyr Asn Arg Pro
                 165                 170
```

( 2 ) INFORMATION FOR SEQ ID NO:63:

( i ) SEQUENCE CHARACTERISTICS:
        ( A ) LENGTH: 150 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( v i ) ORIGINAL SOURCE:

( x i ) SEQUENCE DESCRIPTION: SEQ ID NO:63:

```
Thr Gln Pro Phe Leu His Asp Gly Tyr Ala Val Ser Trp Asn Thr Val
 1               5                  10                  15
Glu Asp Ser Ile Ile Arg Thr Gly Phe Gln Gly Glu Ser Gly His Asp
             20                  25                  30
```

```
Ile  Lys  Ile  Thr  Ala  Glu  Asn  Thr  Pro  Leu  Pro  Ile  Ala  Gly  Val  Leu
     35                       40                      45

Leu  Pro  Thr  Ile  Pro  Gly  Lys  Leu  Asp  Val  Asn  Lys  Ser  Lys  Thr  His
     50                       55                      60

Ile  Ser  Val  Asn  Gly  Arg  Lys  Ile  Arg  Met  Arg  Cys  Arg  Ala  Ile  Asp
65                            70                       75                      80

Gly  Asp  Val  Thr  Phe  Cys  Arg  Pro  Lys  Ser  Pro  Val  Tyr  Val  Gly  Asn
               85                       90                            95

Gly  Val  His  Ala  Asn  Leu  His  Val  Ala  Phe  His  Arg  Ser  Ser  Ser  Glu
               100                      105                      110

Lys  Ile  His  Ser  Asn  Glu  Ile  Ser  Ser  Asp  Ser  Ile  Gly  Val  Leu  Gly
               115                      120                      125

Tyr  Gln  Lys  Thr  Val  Asp  His  Thr  Lys  Val  Asn  Ser  Lys  Leu  Ser  Leu
     130                      135                      140

Phe  Phe  Glu  Ile  Lys  Ser
145                      150
```

( 2 ) INFORMATION FOR SEQ ID NO:64:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:64:

```
Gly  Ala  Asn  Tyr  Ala  Ala  Trp  Ala  Val  Asn  Val  Ala  Gln  Val
1                   5                        10
```

( 2 ) INFORMATION FOR SEQ ID NO:65:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:65:

```
Pro  Val  Phe  Ala
1
```

( 2 ) INFORMATION FOR SEQ ID NO:66:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:66:

Ile Asp Ser Glu Thr Ala Asp Asn
1               5

( 2 ) INFORMATION FOR SEQ ID NO:67:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:67:

Val His His Asn Thr Glu Glu Ile Val Ala Gln Ser Ile Ala Leu Ser
1               5                   10                  15
Ser Leu Met Val Ala Gln Ala Ile Pro Leu Val Gly Glu Leu
            20              25                  30

( 2 ) INFORMATION FOR SEQ ID NO:68:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:68:

Glu Glu Ile Val Ala Gln Ser Ile Ala Leu Ser Ser Leu Met Val Ala
1               5                   10                  15
Gln Ala Ile Pro Leu Val
            20

( 2 ) INFORMATION FOR SEQ ID NO:69:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:69:

His His Asn Thr Glu Glu
1               5

( 2 ) INFORMATION FOR SEQ ID NO:70:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:70:

Gly Glu Leu Val Asp Ile Gly Phe Ala Ala
1               5                   1 0

( 2 ) INFORMATION FOR SEQ ID NO:71:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:71:

Gln Ser Ile Ala Leu Ser Ser Leu Met Val
1               5                   1 0

( 2 ) INFORMATION FOR SEQ ID NO:72:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:72:

Tyr Asn Phe Val Glu Ser Ile Ile Asn Leu Phe Gln Val Val His Asn
 1               5                  10                  15
Ser Tyr Asn ( 2 ) INFORMATION FOR SEQ ID NO:73:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:73:

Arg Pro Ala Tyr Ser Pro Gly His Lys Thr Gln Pro
 1               5                  10

( 2 ) INFORMATION FOR SEQ ID NO:74:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:74:

Glu Ser Gly His Asp Ile Lys Ile Thr Ala
 1               5                  10

( 2 ) INFORMATION FOR SEQ ID NO:75:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:75:

Glu Asn Thr Pro
 1

( 2 ) INFORMATION FOR SEQ ID NO:76:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:76:

Thr Gly Phe Gln Gly
 1               5

( 2 ) INFORMATION FOR SEQ ID NO:77:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:77:

Glu Asn Thr Pro Leu Pro Ile Ala Gly
 1               5

( 2 ) INFORMATION FOR SEQ ID NO:78:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:78:

Gly Val Leu Leu Pro Thr Ile Pro Gly Lys Leu Asp Val
 1               5                   1 0

( 2 ) INFORMATION FOR SEQ ID NO:79:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear (  i  i  ) MOLECULE TYPE: peptide (  i  i  i  ) HYPOTHETICAL: NO (  i  v  ) ANTI-SENSE: NO (  v  ) FRAGMENT TYPE: internal (  v  i  ) ORIGINAL SOURCE:

(  x  i  ) SEQUENCE DESCRIPTION: SEQ ID NO:79:

Asn  Lys  Ser  Lys  Thr
 1                 5